US006764495B2

(12) United States Patent
Lee et al.

(10) Patent No.: US 6,764,495 B2
(45) Date of Patent: Jul. 20, 2004

(54) EXCISIONAL BIOPSY DEVICES AND METHODS

(75) Inventors: Roberta Lee, Redwood City, CA (US); James W. Vetter, Portola Valley, CA (US)

(73) Assignee: Rubicor Medical, Inc., Redwood City, CA (US)

( * ) Notice: Subject to any disclaimer, the term of this patent is extended or adjusted under 35 U.S.C. 154(b) by 63 days.

(21) Appl. No.: 10/098,014

(22) Filed: Mar. 14, 2002

(65) Prior Publication Data

US 2002/0095100 A1 Jul. 18, 2002

Related U.S. Application Data

(62) Division of application No. 09/417,520, filed on Oct. 13, 1999, now Pat. No. 6,423,081, which is a division of application No. 09/146,743, filed on Sep. 3, 1998, now Pat. No. 6,022,362.

(51) Int. Cl.[7] .............................................. A61B 17/22

(52) U.S. Cl. ...................................... 606/159; 600/564

(58) Field of Search ............................... 606/159, 170, 606/167, 180; 600/564–567

(56) References Cited

U.S. PATENT DOCUMENTS

| | | |
|---|---|---|
| 1,813,902 A | 7/1931 | Bovie |
| 2,816,552 A | 12/1957 | Hoffman |
| 3,320,957 A | 5/1967 | Sokolik |
| 3,732,858 A | 5/1973 | Banko |
| 3,749,085 A | 7/1973 | Willson |
| 3,910,279 A | 10/1975 | Okada et al. |
| 3,955,578 A | 5/1976 | Chamness et al. |
| 4,245,653 A | 1/1981 | Weaver |
| 4,347,846 A | 9/1982 | Dormia |
| 4,611,594 A | 9/1986 | Grayhack |
| 4,650,466 A | 3/1987 | Luther |
| 4,890,611 A | 1/1990 | Monfort |

(List continued on next page.)

FOREIGN PATENT DOCUMENTS

| | | |
|---|---|---|
| DE | 197 06 751 A1 | 2/1997 |
| EP | 0472368 B1 | 2/1992 |
| EP | 0829232 A3 | 3/1998 |
| EP | 0908156 A1 | 4/1999 |
| FR | 2 275 226 | 1/1976 |
| GB | 1 331 468 | 9/1973 |

(List continued on next page.)

*Primary Examiner*—Kevin T. Truong
(74) *Attorney, Agent, or Firm*—Young Law Firm, P.C.

(57) ABSTRACT

An excisional biopsy device includes a tubular member having a window near a distal tip thereof; a cutting tool, a distal end of the cutting tool being attached near the distal tip of the tubular member, at least a distal portion of the cutting tool being configured to selectively bow out of the window and to retract within the window; and a tissue collection device externally attached at least to the tubular member, the tissue collection device collecting tissue excised by the cutting tool as the biopsy device is rotated and the cutting tool is bowed. An excisional biopsy method for soft tissue includes the steps of inserting a generally tubular member into the tissue, the tubular member including a cutting tool adapted to selectively bow away from the tubular member and an external tissue collection device near a distal tip of the tubular member; rotating the tubular member; selectively varying a degree of bowing of the cutting tool; collecting tissue severed by the cutting tool in the tissue collection device; and retracting the tubular member from the soft tissue. The tubular member may include an imaging transducer and the method may include the step of displaying information received from the transducer on a display device and the step of varying the degree of bowing of the cutting tool based upon the displayed information from the imaging transducer. Alternatively, the imaging transducer may be disposed within a removable transducer core adapted to fit within the tubular member.

18 Claims, 10 Drawing Sheets

U.S. PATENT DOCUMENTS

| | | |
|---|---|---|
| 4,903,696 A | 2/1990 | Stasz et al. |
| 4,966,604 A | 10/1990 | Reiss |
| 5,071,424 A | 12/1991 | Reger |
| 5,083,570 A | 1/1992 | Mosby |
| 5,100,423 A | 3/1992 | Fearnot |
| 5,147,355 A | 9/1992 | Friedman et al. |
| 5,152,293 A | 10/1992 | Vonesh et al. |
| 5,156,610 A | 10/1992 | Reger |
| 5,174,296 A | 12/1992 | Watanabe et al. |
| 5,176,688 A | 1/1993 | Narayan |
| 5,192,291 A | 3/1993 | Pannek |
| 5,211,651 A | 5/1993 | Reger |
| 5,217,479 A | 6/1993 | Shuler |
| 5,224,488 A | 7/1993 | Neuffer |
| 5,224,945 A | 7/1993 | Pannek, et al. |
| 5,282,484 A | 2/1994 | Reger |
| 5,308,321 A | 5/1994 | Castro |
| 5,318,576 A | 6/1994 | Plassche |
| 5,325,860 A | 7/1994 | Seward et al. |
| 5,415,656 A | 5/1995 | Tihon et al. |
| 5,441,510 A | 8/1995 | Simpson et al. |
| 5,527,326 A | 6/1996 | Hermann |
| 5,554,163 A | 9/1996 | Shturman |
| 5,630,426 A | 5/1997 | Eggers et al. |
| 5,672,172 A | 9/1997 | Zupkas |
| 5,709,697 A | 1/1998 | Ratcliff |
| 5,766,191 A | 6/1998 | Trerotola |
| 5,794,626 A | 8/1998 | Kieturakis |
| 5,895,399 A | 4/1999 | Barbut et al. |
| 5,913,855 A | 6/1999 | Gough et al. |
| 5,928,159 A | 7/1999 | Eggers et al. |
| 5,928,164 A | 7/1999 | Burbank |
| 5,947,964 A | 9/1999 | Eggers et al. |
| 5,954,655 A | 9/1999 | Hussman |
| 5,954,670 A | 9/1999 | Baker |
| 6,015,390 A | 1/2000 | Krag |
| 6,022,362 A | 2/2000 | Lee |
| 6,036,708 A | 3/2000 | Sciver |
| 6,063,082 A | 5/2000 | DeVore |
| 6,080,149 A | 6/2000 | Huang |
| 6,080,151 A | 6/2000 | Swartz et al. |
| 6,096,053 A | 8/2000 | Bates |
| 6,099,534 A | 8/2000 | Bates |
| 6,106,524 A | 8/2000 | Eggers et al. |
| 6,179,860 B1 | 1/2001 | Fulton, III et al. |
| 6,221,006 B1 | 4/2001 | Dubrul et al. |
| 6,238,389 B1 | 5/2001 | Paddock et al. |
| 6,387,056 B1 | 5/2002 | Kieturakis |
| 6,602,204 B2 | 8/2003 | Dubrul et al. |
| 2002/0058885 A1 | 5/2002 | Burbank et al. |

FOREIGN PATENT DOCUMENTS

| | | | | |
|---|---|---|---|---|
| GB | 2311468 | 10/1987 | | |
| GB | 2204496 | 11/1988 | | |
| JP | 61 029 733 | 2/1986 | | |
| NL | 1.004723 | 6/1998 | | |
| NZ | 202965 | 9/1985 | | |
| SU | 1235497 | 6/1986 | | |
| SU | 1355266 | 11/1987 | | |
| WO | WO 92/20291 | 11/1992 | | |
| WO | WO 95/02370 | 1/1995 | | |
| WO | WO 95/02371 | 1/1995 | | |
| WO | WO 96/29946 | 10/1996 | | |
| WO | WO 98/08441 | 3/1998 | | |
| WO | WO 99/01074 | 1/1999 | | |
| WO | WO 99/04704 | 2/1999 | | |
| WO | WO 99/43262 | 9/1999 | | |
| WO | WO99/44506 | * 9/1999 | | 606/180 |
| WO | WO 99/44506 | 10/1999 | | |
| WO | WO 99/53851 | 10/1999 | | |
| WO | WO 00/10471 | 3/2000 | | |
| WO | WO 00/12009 | 3/2000 | | |
| WO | WO 00/16697 | 3/2000 | | |
| WO | WO 00/30531 | 6/2000 | | |
| WO | WO 00/33743 | 6/2000 | | |
| WO | WO 00/44295 | 8/2000 | | |
| WO | WO 00/45854 | 8/2000 | | |
| WO | WO 00/74561 | 12/2000 | | |
| WO | WO 01/28445 | 4/2001 | | |
| WO | WO 01/28446 | 4/2001 | | |

* cited by examiner

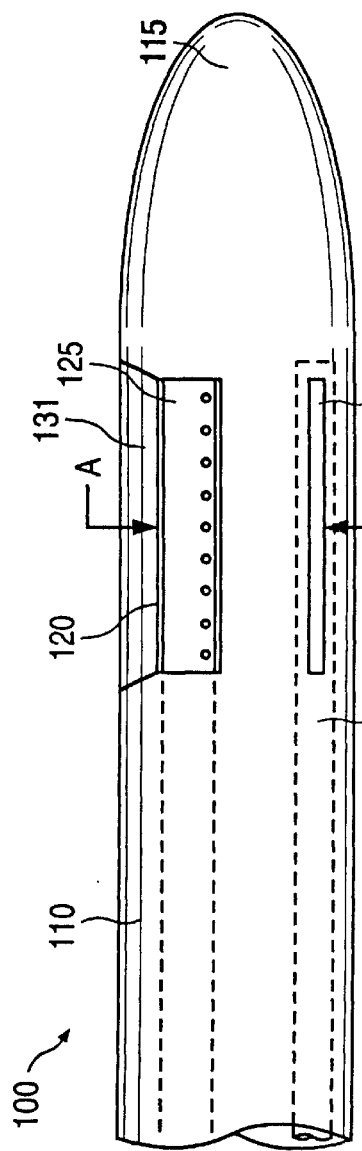
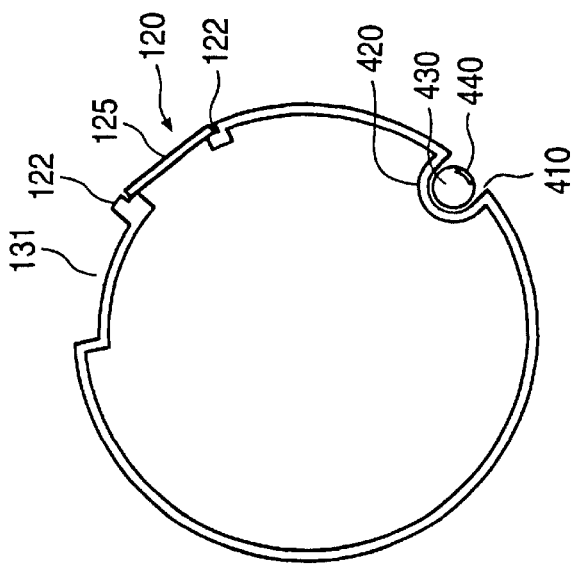
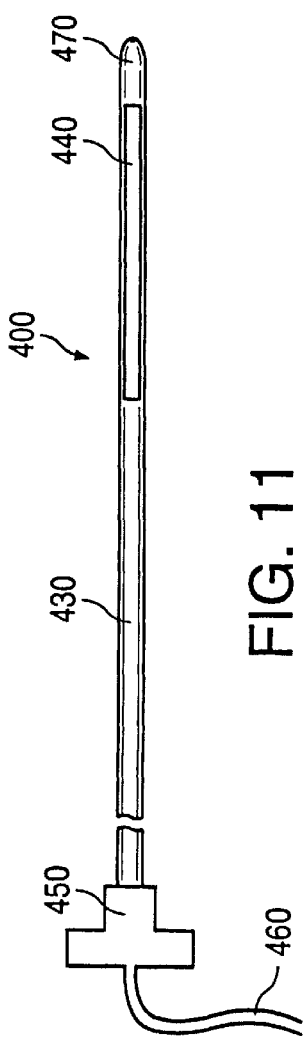
FIG. 10
FIG. 12
FIG. 11

EXCISIONAL BIOPSY DEVICES AND METHODS

CROSS-REFERENCE TO RELATED APPLICATIONS

The present application is a Divisional of U.S. Ser. No. 09/417,520, filed Oct. 13, 1999, now U.S. Pat. No. 6,423,081 which is a Divisional of U.S. Ser. No. 09/146,743, filed Sep. 3, 1998 now U.S. Pat. No. 6,022,362.

BACKGROUND OF THE INVENTION

1. Field of the Invention

The present invention pertains to the field of soft tissue excisional biopsy devices and methods. In particular, the present invention relates to the field of devices and methods for excising suspicious lesions from soft tissue, such as breast tissue.

2. Description of the Related Art

Breast cancer is a major threat and concern to women. Early detection and treatment of suspicious or cancerous lesions in the breast has been shown to improve long term survival of the patient. The trend is, therefore, to encourage women not only to perform monthly self-breast examination and obtain a yearly breast examination by a qualified physician, but also to undergo annual screening mammography commencing at age 40. Mammography is the only screening modality available today that can detect small, nonpalpable lesions. These nonpalpable lesions may appear as opaque densities relative to normal breast parenchyma and fat or as clusters of microcalcifications.

The conventional method for diagnosing, localizing and excising nonpalpable lesions detected by mammography generally involves a time-consuming, multi-step process. First, the patient goes to the radiology department where the radiologist finds and localizes the lesion either using mammography or ultrasound guidance. Once localized, a radio-opaque wire is inserted into the breast. The distal end of the wire may include a small hook or loop. Ideally, this is placed adjacent to the suspicious area to be biopsied. The patient is then transported to the operating room. Under general or local anesthesia, the surgeon performs a procedure called a needle-localized breast biopsy. In the needle-localized breast biopsy, the surgeon, guided by the wire previously placed in the patient's breast, excises a mass of tissue around the distal end of the wire. The specimen is sent to the radiology department where a specimen radiograph is taken to confirm that the suspicious lesion is contained within the excised specimen. Meanwhile, the surgeon, patient, anesthesiologist and operating room staff, wait in the operating room for confirmation of that fact from the radiologist before the operation is completed. The suspicious lesion should ideally be excised in toto with a small margin or rim of normal breast tissue on all sides. Obtaining good margins of normal tissue is extremely dependent upon the skill and experience of the surgeon, and often an excessively large amount of normal breast tissue is removed to ensure that the lesion is located within the specimen. This increases the risk of post-operative complications, including bleeding and permanent breast deformity. As 80% of breast biopsies today are benign, many women unnecessarily suffer from permanent scarring and deformity from such benign breast biopsies.

More recently, less invasive techniques have been developed to sample or biopsy the suspicious lesions to obtain a histological diagnosis. The simplest of the newer techniques is to attempt visualization of the lesion by external ultrasound. If seen by external ultrasound, the lesion can be biopsied while being continuously visualized. This technique allows the physician to see the biopsy needle as it actually enters the lesion, thus ensuring that the correct area is sampled. Current sampling systems for use with external ultrasound guidance include a fine needle aspirate, core needle biopsy or vacuum-assisted biopsy devices.

Another conventional technique localizes the suspicious lesion using stereotactic digital mammography. The patient is placed prone on a special table that includes a hole to allow the designated breast to dangle therethrough. The breast is compressed between two mammography plates, which stabilizes the breast to be biopsied and allows the digital mammograms to be taken. At least two images are taken 30 degrees apart to obtain stereotactic views. The x, y and z coordinates targeting the lesion are calculated by a computer. The physician then aligns a special mechanical stage mounted under the table that places the biopsy device into the breast to obtain the sample or samples. There are believed to be three methods available to biopsy lesions using a stereotactic table: (1) fine needle aspiration, (2) core needle biopsy and (3) vacuum-assisted core needle biopsy.

Fine needle aspiration uses a small gauge needle, usually 20 to 25 gauge, to aspirate a small sample of cells from the lesion or suspicious area. The sample is smeared onto slides that are stained and examined by a cytopathologist. In this technique, individual cells in the smears are examined, and tissue architecture or histology is generally not preserved. Fine needle aspiration is also very dependent upon the skill and experience of the operator and can result in a high non-diagnostic rate (up to about 83%), due to inadequate sample collection or preparation.

Core needle biopsy uses a larger size needle, usually 14 gauge to sample the lesion. Tissue architecture and histology are preserved with this method. A side-cutting device, consisting of an inner trough with an outer cutting cannula is attached to a spring-loaded device for a rapid semi-automated firing action. After the lesion is localized, local anaesthetic is instilled and a small incision is made in the skin with a scalpel. The device enters the breast and the needle tip is guided into the breast up to the targeted lesion. The device is fired. First, the inner cannula containing the trough rapidly penetrates the lesion. Immediately following this, the outer cutting cannula rapidly advances over the inner cannula cutting a sample of tissue off in the trough. The whole device is then removed and the sample retrieved. Multiple penetrations of the core needle through the breast and into the lesion are required to obtain an adequate sampling of the lesion. Over 10 samples have been recommended by some.

The vacuum-assisted breast biopsy system is a larger semi-automated side-cutting device. It is usually 11 gauge in diameter and is more sophisticated than the core needle biopsy device. Multiple large samples can be obtained from the lesion without having to reinsert the needle each time. A vacuum is added to suck the tissue into the trough. The rapid firing action of the spring-loaded core needle device is replaced with an oscillating outer cannula that cuts the breast tissue off in the trough. The physician controls the speed at which the outer cannula advances over the trough and can rotate the alignment of the trough in a clockwise fashion to obtain multiple samples.

If a fine needle aspirate, needle core biopsy or vacuum-assisted biopsy shows malignancy or a specific benign diagnosis of atypical hyperplasia, then the patient needs to undergo another procedure, the traditional needle-localized breast biopsy, to fully excise the area with an adequate margin of normal breast tissue. Sometimes the vacuum-assisted device removes the whole targeted lesion. If this occurs, a small titanium clip should be placed in the biopsy field. This clip marks the area if a needle-localized breast biopsy is subsequently required for the previously mentioned reasons.

Another method of biopsying the suspicious lesion utilizes a large end-cutting core device measuring 0.5 cm to 2.0 cm in diameter. This also uses the stereotactic table for stabilization and localization. After the lesion coordinates are calculated and local anesthesia instilled, an incision large enough is permit entry of the bore is made at the entry site with a scalpel. The breast tissue is cored down to and past the lesion. Once the specimen is retrieved, the patient is turned onto her back and the surgeon cauterizes bleeding vessels under direct vision. The incision, measuring 0.5 to larger than 2.0 cm is sutured closed.

The stereotactic table requires awkward positioning of the patient and may be extremely uncomfortable. The woman must lie prone during the entire procedure, which may be impossible for some patients. In addition, the lesion to be biopsied must be in the center working area of the mammography plates. This may be extremely difficult and uncomfortable for the patient if the lesion is very posterior near the chest wall or high towards the axilla.

The woman is subjected to increased radiation exposure as multiple radiographs are required throughout the course of the procedure to: (1) confirm that the lesion is within the working area of the mammography plates, (2) obtain the stereotactic coordinates (at least two views), (3) verify the positioning of the biopsy needle prior to obtaining tissue, and (4) verify that the lesion was indeed sampled. If any difficulty is encountered during the procedure, additional radiographic exposures are required to verify correction of the problem.

Using the core needle biopsy or vacuum-assisted device, bleeding is controlled only by manual pressure. Bleeding is generally not an issue with fine needle aspiration, but is a legitimate complication of the former two methods. Ecchymoses, breast edema and hematomas can occur. This causes increased post-procedural pain and delays healing. Rarely, the patient may require an emergency operation to control and evacuate a tense hematoma.

Another major concern is the possibility of tumor dissemination. The core needle biopsy and vacuum-assisted devices both cut into the tumor and carve out multiple samples for examination. While cutting into the tumor, cancerous cells may be dislodged. Cutting across blood vessels at the same time may allow the freed cancerous cells access to the blood stream, thus possibly seeding the tumor beyond its original locus. The long-term consequences of tumor seeding with the risk of bloodborne metastases are unknown at this time, as the techniques are relatively new. However, documented instances of cancerous cells seeding locally into needle tracks exist. There are numerous reports of metastases growing in needle tracks from previous biopsies of a cancerous mass. Most of these are from lung or liver cancers. However, at least one case of mucinous carcinoma of the breast growing in a needle track has been reported. The long-term consequences of neoplasm seeding into needle tracks are currently unknown, again because the techniques are relatively new. Some recommend excision of the entire needle track, including the skin entry site, during the definitive surgical procedure for a diagnosed cancer, whether it be a lumpectomy or a mastectomy. Others assume that with a lumpectomy, the post-operative radiation therapy will destroy any displaced cancer cells in the needle track. With the trend towards treating very small cancers only by excision and without a post-excision course of radiation therapy, the risk of cancer cells metastasizing and growing in needle tracks is very real.

The large core cutting device (0.5 cm to 2.0 cm) generally eliminates the risk of needle track seeding as it is designed to excise the lesion intact. A stereotactic table is required with the same inherent awkwardness for the patient, as discussed above. Bleeding is controlled, albeit manually, requiring that the patient wait until the end of the procedure to be turned over. Compression is used to stabilize the breast and localize the lesions. The breast, however, may be torqued and distorted between the compression plates such that when the plates are removed after the biopsy, the large core track left behind may not be straight, but actually tortuous. This can result in permanent breast deformity.

The location of the insertion site into the breast is dictated by the positioning of the breast in the machine and not by the physician. The entry site is usually away from the nipple-areolar complex and is usually located on the more exposed areas of the breast. For the fine needle aspirate, core biopsy and vacuum-assisted devices, the incision is usually very small and the scar almost unappreciable. However, in the case of the large core biopsy device (0.5 to 2.0 cm), a large incision is needed. Such a large incision often results in a non-aesthetically placed scar.

The newer conventional minimally invasive breast biopsy devices have improved in some ways the ability to diagnose mammographically detected nonpalpable lesions. These devices give the patient a choice as to how she wants the diagnosis to be made. Moreover, these devices are substantially less expensive than the older traditional needle-localized breast biopsy. They are not, however, the final solution. Due to the above-discussed problems and risks associated with compression, needle-track seeding, blood borne metastases, bleeding, radiation exposure and awkwardness of the stereotactic table, more refined devices and methods are needed to resolve these issues. Also, the conventional biopsy devices do not consider margins in their excisions and if cancer is diagnosed, the patient must undergo a needle-localized breast lumpectomy to ensure that adequate margins are removed around the cancer. Devices and methods, therefore, must address the problem of obtaining adequate margins so that a second procedure is not required. Margins, moreover, cannot be assessed while the breast is being compressed.

SUMMARY OF THE INVENTION

It is, therefore, an object of the present invention to provide devices and methods to efficiently and safely excise suspicious lesions from the breast. It is also an object of the present invention to provide devices and methods that remove the entire lesion intact with the minimum amount of normal tissue surrounding the lesion needed to provide adequate margins. It is a further object of the present invention to provide devices and methods that provide hemostasis in the breast to minimize complications of ecchymosis, hematoma formation, and breast edema. It is another object of the present invention to provide methods and devices to provide intra-tissue ultrasonic guidance to provide real time, in situ monitoring of the procedure. A still further object is to provide devices and methods that allow the physician to minimize the size of the incision though which the procedure is performed and to leave an aesthetically acceptable scar on the breast.

In accordance with the above-described objects and those that will be mentioned and will become apparent below, an embodiment of an excisional biopsy device according to the present invention comprises:

a tubular member having a window near a distal tip thereof;

a cutting tool, a distal end of the cutting tool being attached near the distal tip of the tubular member, at least a distal portion of the cutting tool being configured to selectively bow out of the window and to retract within the window; and a tissue collection device externally attached at least to the tubular member, the tissue collection device being adapted to collect a tissue sample severed by the cutting tool as the biopsy device is rotated and the cutting tool is bowed.

According to further embodiments, the distal portion of the cutting tool may comprise a thin ribbon sharpened on a leading edge thereof. The leading edge of the thin ribbon may be serrated. The tubular member may comprise an internal guide allowing a proximal portion of the cutting tool to slide therein when a proximal end of the cutting tool is pushed in a distal direction or pulled in a proximal direction. The cutting tool may further comprise an interior lumen; and a plurality of through holes in the distal portion thereof, the through holes being in fluid communication with the interior lumen. The tissue collection device may comprise a bag within which the excised sample of tissue is collected. An opening of the bag may be at least co-extensive with the window in the tubular member. The tissue collection device may be configured to open and to close as the cutting tool is selectively bowed and retracted, respectively. The tissue collection device may comprise a bag attached to the tubular member and to a trailing edge of the distal portion of the cutting tool, the bag opening and closing as the cutting tool is bowed and retracted, respectively. An ultrasound sensor may be mounted within the distal portion of the tubular member, the ultrasound sensor being disposed within the tubular member so as to image tissue about to be cut by the cutting tool as the biopsy device is rotated. The ultrasound sensor may be electrically connected to at one or more data processing and display devices to allow either a real time or a near real time graphical representation of the tissue to be cut. The distal portion of the cutting tool may be electrically connected to an RF or other power source. The distal portion of the cutting tool may comprise a thin wire.

An invasive interventional device for soft biological tissue, according to a further embodiment of the present invention, comprises a rotatable tubular member having a distal tip adapted to penetrate the tissue;

a work element disposed near the distal tip of the tubular member, the work element acting upon the tissue coming into contact therewith as the tubular member rotates;

an ultrasound transducer disposed near the distal tip of the tubular member and away from the work element, so that the transducer sweeps a plane within the tissue ahead of the work element as the tubular member rotates; and means for controlling an operation of the work element based upon information gathered from the ultrasound transducer.

According to still further embodiments, the ultrasound transducer may be tuned within a range from about 7.5 MHz to about 20 MHz. The ultrasound transducer may be disposed within the tubular member at an angle a relative to the work element, the angle a being no smaller than that necessary to effectively control the operation of the work element in response to the information gathered from the transducer as the tubular member rotates. The angle a is preferably less than about 180 degrees. The work element may comprise at least one device selected from the group consisting of: an abrasive device, a reciprocating cutting device, a bowing cutting device, an electrosurgical device, a laser device and a vibrating device. The ultrasonic transducer may be connected to at least one data processing and display device to allow an operator of the device to ascertain a structure of the tissue and to control the operation of the work element before the tissue comes into contact with the work element as the device rotates. The work element may comprise a cutting tool, a distal end of the cutting tool being attached near the distal tip of the tubular member, at least a distal portion of the cutting tool being configured to selectively bow out of a window in the tubular member and to retract within the window. The controlling means may include means for selectively bowing and retracting the cutting tool.

According to yet another embodiment, an excisional biopsy method for soft tissue, according to the present invention, comprises the steps of:

inserting a generally tubular member into the tissue, the tubular member including a cutting tool adapted to selectively bow away from the tubular member and an external tissue collection device near a distal tip of the tubular member;

rotating the tubular member;

selectively varying a degree of bowing of the cutting tool;

collecting tissue severed by the cutting tool in the tissue collection device; and retracting the tubular member from the soft tissue.

The rotating step may be carried out by manually rotating the tubular member. The tubular member may further include an imaging transducer and the method may further include the steps of displaying information received from the transducer on a display device; and varying the degree of bowing of the cutting tool based upon the displayed information from the imaging transducer. The cutting tool may comprise an electrosurgical blade and the method may further comprise the step of varying the power (for example, RF power) applied to the electrosurgical blade based upon information received from the transducer. A step of stabilizing the soft tissue in an uncompressed state prior to the inserting step may also be carried out. A step of controlling the cutting tool to assume a non-extended state may be carried out prior to the inserting step and before the retraction step. The tissue collection device assumes a closed configuration when the cutting tool assumes the non-extended state. The extension of the cutting tool may be controlled by selectively and manually pushing and retracting a proximal end of the cutting tool in the distal and proximal directions, respectively. The cutting tool may comprise an interior lumen and a plurality of through holes in fluid communication therewith, and the method may further comprise the step of delivering at least one fluid to the tissue via the plurality of through holes.

The present invention may also be viewed as an imaging and treatment method for soft tissue, comprising the steps of:

inserting a tubular member into the soft tissue, the tubular member including an ultrasonic transducer mounted near a distal end of the tubular member;

rotating the tubular member within the soft tissue;

displaying an output of the ultrasonic transducer on a display device; and acting upon the soft tissue based upon the displayed output.

According to further preferred embodiments, the ultrasonic transducer may be tuned to within a frequency range of between about 7.5 MHz to about 20 MHz. The acting step may include a step of severing a selectively variable volume of soft tissue from a main tissue mass. A step of collecting the severed volume of tissue in a tissue collection device mounted externally to the tubular member may also be carried out.

According to a further embodiment, an excisional biopsy device, according to the present invention, comprises:

a tubular member having a first and a second window near a distal tip thereof;

a cutting tool configured to selectively bow out of the first window and to retract within the first window; and a removable transducer core, the transducer core including an active transducer element configured to face out of the second window when the removable transducer core is fitted within the tubular member.

The removable core may be adapted to snap fit within the tubular member. The active transducer element may, for example, include an ultrasound transducer. The removable transducer core may include a tapered distal tip configured to readily penetrate soft tissue. An external tissue collection device may be attached to the cutting tool and/or to the tubular member. The tubular member may further comprise a recessed section adjacent a trailing edge of the cutting tool, the recessed section being adapted to receive the external tissue collection device. An expandable sheath may also be included, the expandable sheath being adapted to receive the removable transducer core and the tubular member.

The present invention may also be viewed as a method of excising a lesion from soft biological tissue using an excisional biopsy system including a generally tubular member having a cutting tool, a removable transducer core adapted to fit within the tubular member and an expandable sheath, comprising the steps of:

fitting the transducer core through the expandable sheath, inserting the transducer and sheath though an incision in the tissue;

imaging a target site within the tissue by energizing the transducer core, removing the transducer core from sheath while leaving the sheath in place within the tissue;

securing the core within the generally tubular member so the core faces outwardly from the tubular member;

sliding the tubular member through the expandable sheath until the cutting tool is positioned adjacent the lesion;

cutting the lesion with the cutting tool; and retracting at least the tubular member from the incision.

A step of stabilizing the breast in one of an uncompressed and a slightly expanded state prior to the inserting step may also be carried out. The sheath may remain within the tissue after the retracting step and the method may further comprise the step of re-inserting the transducer core within the sheath and imaging the target site to insure that the lesion has been excised. A step of collecting the cut lesion within an external tissue collection device secured to the tubular member may also be carried out. Both the tubular member and the sheath may be retracted from the incision.

The present invention may also be viewed as an excisional biopsy device, comprising:

a single use disposable tubular member having a window near a distal tip thereof, the tubular member including a cutting tool, a distal end of the cutting tool being attached near the distal tip of the tubular member, at least a distal portion of the cutting tool being configured to selectively bow out of the window and to retract within the window; and a single use disposable tissue collection device externally attached at least to the tubular member, the tissue collection device collecting tissue severed by the cutting tool as the biopsy device is rotated and the cutting tool is bowed.

In yet another embodiment, the present invention is an excisional biopsy device, comprising:

a single use disposable tubular member having a first and a second window near a distal tip thereof, the tubular member including a cutting tool configured to selectively bow out of the first window and to retract within the first window; and a removable transducer core, the transducer core including an active transducer element configured to face out of the second window when the removable transducer core is fitted within the tubular member.

BRIEF DESCRIPTION OF THE DRAWINGS

For a further understanding of the objects and advantages of the present invention, reference should be made to the following detailed description, taken in conjunction with the accompanying figures, in which:

FIG. 10 shows another embodiment of the present invention, equipped with a removable transducer core.

FIG. 11 shows a transducer core suitable for the embodiment of FIG. 10.

FIG. 12 is a cross-sectional view of FIG. 10, taken along line AA'.

DESCRIPTION OF THE PREFERRED EMBODIMENTS

Figure 1A:
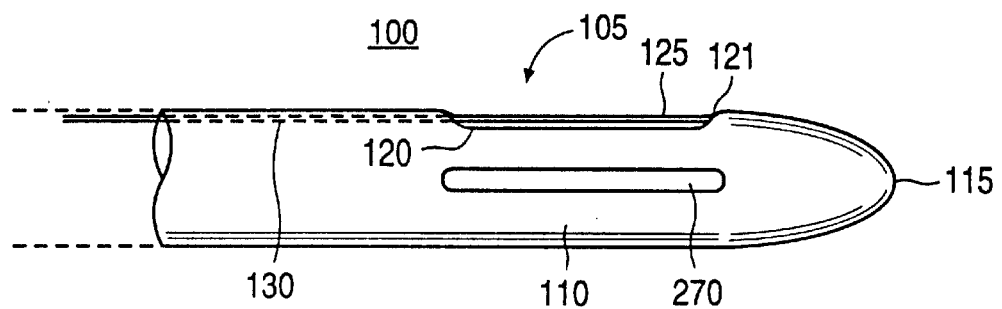
FIG. 1A shows an embodiment of the excisional device according to the present invention with the cutting tool in its flat, retracted configuration.
Figure 1B:
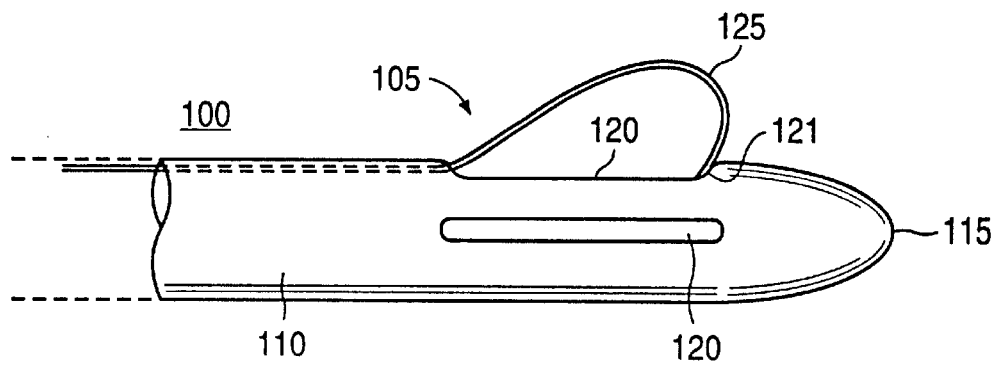
FIG. 1B shows the excisional device of FIG. 1A with its cutting tool in an extended, bowed configuration.
Figure 1C:
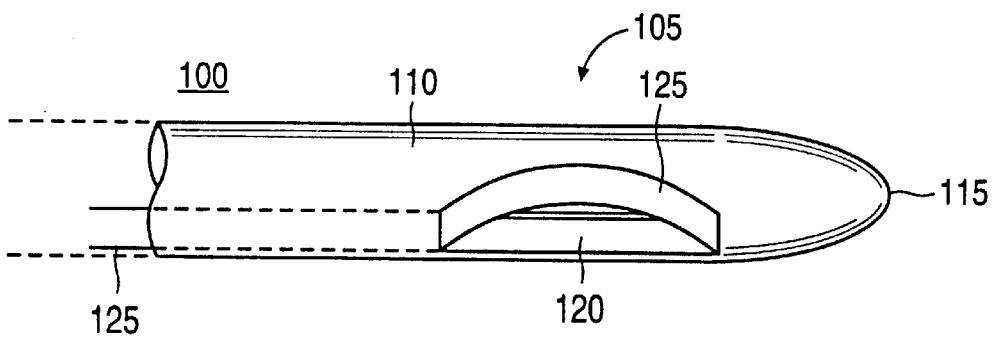
FIG. 1C shows another view of the excisional device of FIG. 1A.

FIGS. 1A, 1B and 1C show an embodiment of the distal region 105 of the excisional biopsy device 100 according to the present invention. Considering FIGS. 1A, 1B and 1C collectively, the distal region 105 of the excisional biopsy device 100 includes a generally tubular member 110 having a generally tapered distal tip 115. The distal tip 115 is configured to penetrate soft tissue, such as breast tissue, lung tissue, liver tissue and the like. Preferably, therefore, the distal tip 115 and the distal region 105 of the excisional biopsy device 100 present a smooth, and relatively atraumatic profile to the soft tissue in which it is designed to penetrate. Alternatively, the tip 115 may be sharply pointed and/or may include an energy source (not shown) to facilitate cutting through the tissue. The tubular member 110 may be formed of rigid and hard plastic, or may be made of stainless steel, for example. Preferably, the tubular member 100 is used once and disposed of, for both safety and functional reasons.

Figure 2A:
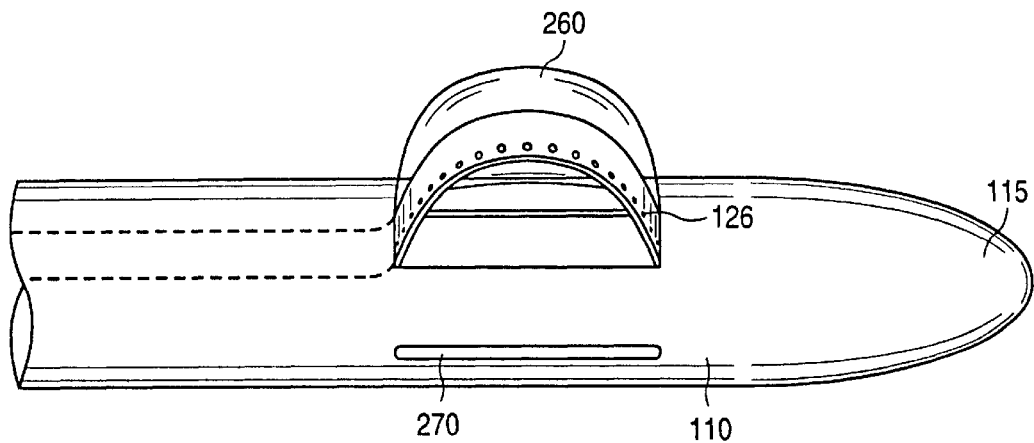
FIG. 2A depicts the distal region of another embodiment of the excisional device according to the present invention, showing the excisional device together with the external tissue collection attached thereto in the open configuration.
Figure 2B:
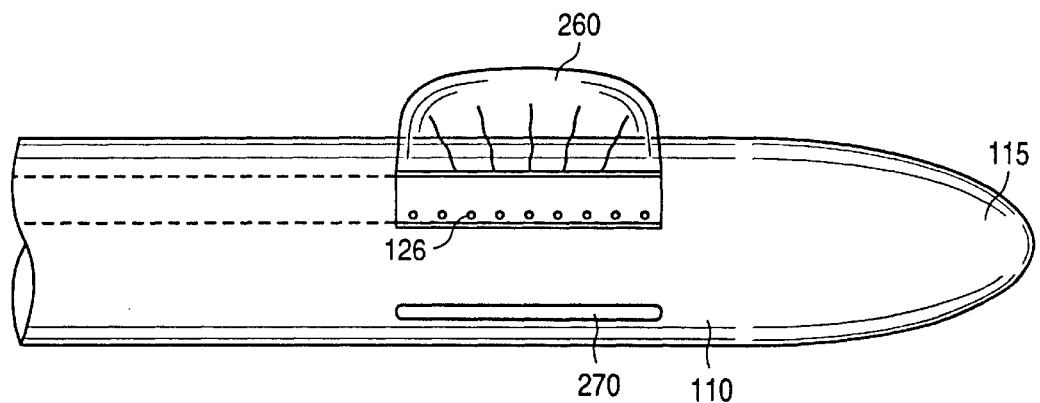
FIG. 2B shows the excisional device of FIG. 2A together with the external tissue collection attached thereto in the closed configuration.
Figure 2C:
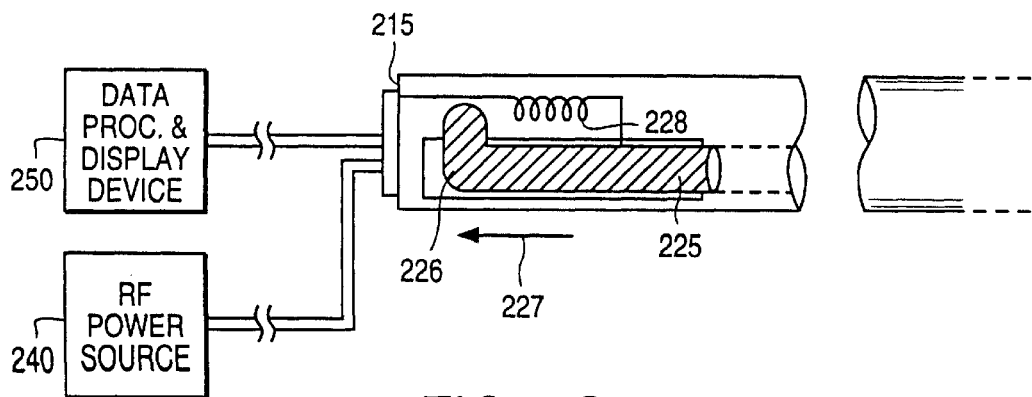
FIG. 2C shows an embodiment of the proximal region of the excisional device according to the present invention.

A cutter window 120 is disposed within the tubular member 110. The cutter window 120 may be, for example, a shallow trench formed in the tubular member 110. As best seen in FIG. 1C, the cutter window 120 may be a shallow and substantially rectangular trench in the tubular member 110, or may be, for example, a thin, shallow I-shaped trench. The excisional biopsy device 125 includes a work element, such as a cutting tool 125. The distal end of the cutting tool 125 is attached to the tubular member 110 near its distal tip 115. For example, the distal end of the cutting tool 125 may be attached to the distal-most point 121 of the cutter window 120. The cutting tool 125, however, may alternatively be attached to other points within the distal region 105. The distal portion of the cutting tool 125 is exposed through the cutter window 120. The remaining portion of the cutting tool 125 is disposed within an internal guide or lumen 130 of the generally tubular member 110. The internal guide 130 constrains the movement of the cutting tool 125 and allows the cutting tool 125 to freely slide therein, parallel to the longitudinal axis of the tubular member 110. With particular reference now to FIG. 2C, the proximal portion 225 of the cutting tool 125 emerges from the internal lumen 130 near the proximal end 215 of the tubular member 110. The proximal end of the cutting tool 125 may, for example, include a push or turn knob 226. The push or turn knob 226 allows the operator of the excisional biopsy device 100 to selectively push the cutting tool 125 in the distal direction (away from the physician and toward the distal tip 115) or retract the cutting tool 125 in the proximal direction (toward the physician and away from the distal tip 115). To assist in controlling the movement of the cutting tool 125, the cutting tool is preferably biased in the proximal direction, as symbolized by the arrow 227 in FIG. 2C. This biasing may be effectuated by means of a spring 228 attached at or near the proximal end 215 of the tubular member 110 and to the proximal portion 225 of the cutting tool 125. In this manner, the default configuration of the cutting tool 125 is the retracted position, wherein the cutting tool 125 lies substantially flat within the cutter window 120 of the tubular member 110.

The cutting tool 125, when pushed in the distal direction by the physician applying pressure in the distal direction on the push or turn knob 226 or equivalent structure, slides within the internal guide 130 of the tubular member 110. As the distal end of the cutting tool 125 is attached near the distal end of the tubular member 110 or to the distal-most point 121 of the cutter window 120, the portion thereof exposed through the cutter window 120 tends to bow outwardly, extending out of the cutter window 120, as shown in FIG. 1B. The extension out of the cutter window 120 and the degree of bowing may be controlled by the physician, by appropriate action on the push or turn knob 226. Thus, the possible range of extension and bowing is potentially infinite, being limited only by the physician's ability to control the cutting tool 125 by finely pushing and retracting the push or turn knob 226. The degree of extension, as well as the shape of the bowed portion of the cutting tool, therefore, may be controlled by selectively sliding the cutting tool within the internal guide 130 of the tubular member 110.

The shape of the bowed portion and the ease with which the distal portion of the cutting tool 125 bows outwardly may be varied by varying the physical characteristics of the cutting tool 125. Preferably, the cutting tool is formed of a resilient, readily deformable material that, when unstressed, returns to its original unbiased configuration. For example, a nickel titanium alloy may be used for the cutting tool 125, to allow the cutting tool 125 to exhibit shape-memory characteristics. The shape of the cutting tool 125 in its bowed and extended configuration (FIG. 2) may be further controlled by varying, for example, the thickness of the cutting tool over the portion thereof exposed through the cutter window 120. A locally thicker portion of the cutting tool 125 will not bend as readily as a locally relatively thinner portion thereof. Judiciously varying the thickness, for example, of the cutting tool 125, therefore, allows the curvature of the bowed portion thereof to be controlled.

As shown in FIGS. 1A, 1B, and with reference to FIG. 1C, pushing on the push or turn knob 226 (or any such functionally equivalent structure) causes the cutting tool 125 to bow outwardly and extend out from the cutter window 120 of the tubular member 110, as shown in FIG. 1B. Similarly, retracting the push or turn knob 226 (or any such functionally equivalent structure) causes the cutting tool 125 to flatten out within the cutter window 120 and to assume a configuration (shown in FIG. 1A) that may be substantially flush with the outer surface of the tubular member 110. In this configuration, the tubular member 110 may easily penetrate soft tissue, such as breast, lung, liver or other soft body tissue.

In operation, the surgeon makes an incision into the patient's skin, such as the surface of the breast. The excisional biopsy device 100 then may be directly introduced into the breast tissue, or an expandable sheath (shown at reference numeral 495 in FIG. 13) may be introduced into the incision and thereafter expanded as the excisional biopsy device 100 is introduced therein. In any event, the excisional biopsy device is introduced into the breast tissue itself and positioned, for example, adjacent to the lesion in the breast or adjacent the target site from which the excision is to take place. During the introduction of the excisional biopsy device 100 into the soft tissue, the cutting tool 125 is in its retracted configuration wherein the portion thereof exposed through the cutter window 120 is substantially flat. The excisional device 100, in this configuration, therefore, exhibits a smooth and tapered profile to the surrounding tissue. Once the device 100 has been determined to have been properly positioned within the soft tissue, the device is rotated about its longitudinal axis. The rotation may be carried out manually, or the rotation of the device may be carried out by a motorized unit disposed within the proximal region of the device 100. As the device 100 rotates, the surgeon causes the cutting tool 125 to bow outwardly and to extend from the cutter window 120. Preferably, the degree of bowing and outward extension is at least sufficient to include the lesion (such as the targeted microcalcification within the breast) within the space between the cutter window 120 and the cutting tool 125. The cutting tool 125 cuts the tissue as the device 100 is rotated, thereby severing the lesion from its surrounding breast tissue mass. By completing at least one revolution within the breast tissue, the cutting tool 125 sweeps a volume of revolution of breast tissue and severs that volume from the main tissue mass. Such volume of revolution includes at least the targeted lesion. Preferably, the volume of revolution severed from the main tissue mass not only includes the targeted lesion, but also includes a margin of healthy tissue surrounding the lesion. The degree of extension and bowing of the cutting tool 125 may be varied within a given revolution of the excisional biopsy device 100. In this manner, it is possible to exert fine control over the amount of tissue cut away from the main tissue mass, as well as fine control over the shape of the severed mass.

After the lesion and preferably a margin of healthy tissue around the lesion have been severed, the severed tissue may be removed from the main tissue mass. This removal of the severed tissue may be effectuated by any number of means, including the retraction of the excisional biopsy device 100 from the main tissue mass. Alternately, severed tissue extraction may be carried out by means of the structure and method to be described below.

Figure 4:
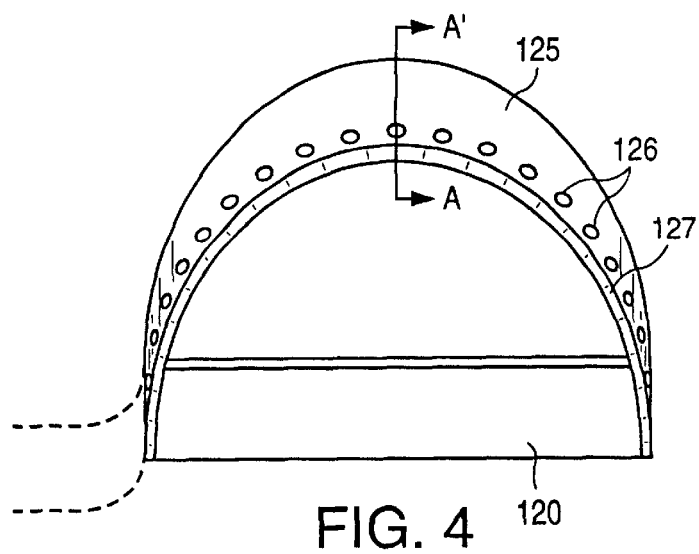
FIG. 4 shows a detailed view of a cutting tool suitable for use with the excisional device according to the present invention.

The cutting tool 125 may, as shown in FIG. 1C, be configured as a thin ribbon. The thin ribbon 125 shown in FIG. 1C is preferably sharpened on its leading edge to facilitate cutting through tissue and sometimes fibrous and calcified masses. The leading edge of the cutting tool 125 is that edge thereof that first comes into contact with the tissue to be severed as the device 100 is rotated. Such a sharpened leading edge is shown in FIG. 4 at reference numeral 127. The width of such a ribbon cutting tool 125 is preferably smaller than the width of the cutter window 120 into which it recedes when the cutting tool 125 is retracted in the proximal direction.

Figure 8:
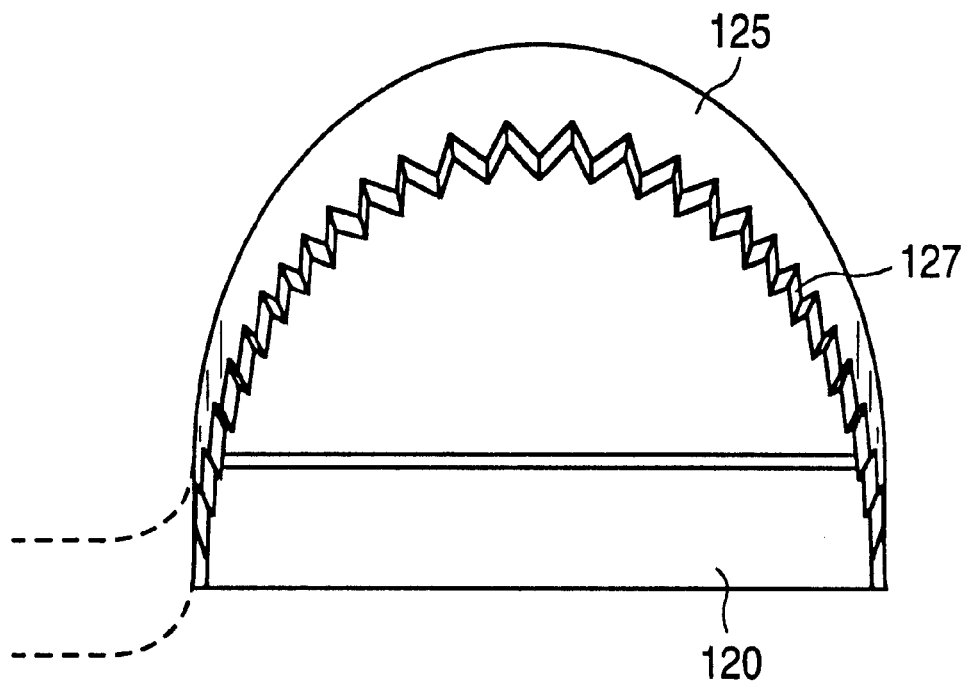
FIG. 8 shows another embodiment of a cutting tool suitable for use with the excisional biopsy device according to the present invention.

Another embodiment of the cutting tool 125 is shown in FIG. 8. To decrease the forward resistance of the cutting tool 125 as it slowly cuts through tissue, the leading edge of the portion thereof exposed through the cutter window 120 may be serrated, including a plurality of teeth 127. In turn, the leading edge of the plurality of teeth 127 may include a sharpened edge. In this manner, as the excisional device 100 rotates, only the forward-most tips of the teeth 127 will initially come into contact with the tissue to be cut, thus reducing the tissue surface upon which the force of the rotating cutting blade 125 is applied. Thus, the cutting blade 125 of FIG. 8 is believed to be highly effective in cutting through even relatively dense or fibrous tissue while minimizing the torque to be applied to the excisional biopsy device 100 as it is caused to rotate within the main soft tissue mass.

Figure 5:
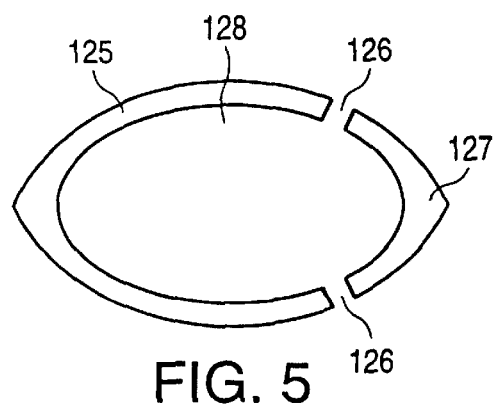
FIG. 5 shows a cross section of the cutting tool, taken along line AA' in FIG. 4.

Referring to FIG. 4 and also to FIG. 5, the cutting tool 125 may further comprise an interior lumen 128 running an entire length or a portion of the length of the cutting tool 125. The cutting tool 125 may further include a plurality of through holes 126 in the distal portion of the cutting tool 125 exposed through the cutter window 120. The plurality of through holes 126 are in fluid communication with the internal lumen 128. In use, the internal lumen 128 may be connected, in the proximal portion of the excisional biopsy device 100, to a fluid reservoir. The fluid reservoir, which may be internal or external to the proximal section of the device 100, supplies the distal portion of the cutting tool 125 with, for example, anaesthetic (such as, for example, lidocaine) and/or antibiotic fluid. In this manner, such anaesthetic and/or antibiotic fluid (or other fluid) may be delivered precisely to the tissue surrounding the cutting tool 125 as it rotates. A precisely dosed anaesthetic, for example, may be delivered to the very site where it is most needed. As such anaesthetic is delivered only where it is needed, the effect thereof is near instantaneous, and the patient feels little or no pain as the excisional biopsy device 100 according to the present invention is rotated within her breast, or other soft tissue. FIG. 5 shows a cross-section of the cutting tool 125 of FIG. 4, taken along line AA' in FIG. 4.

Care should be exercised in selecting the configuration and materials for the cutting tool 125 shown in FIGS. 4 and 5. Indeed, the configuration and materials selected should allow the cutting tool 125 to bow and extend out of the cutter window 120 of the device 100 without, however, pinching or substantially disrupting the flow of fluid delivered via the internal lumen 128 of the cutting tool 125, if the cutting tool 125 is provided with such. For example, the cutting tool 125 may be made of a shape-memory metal, such as nickel-titanium and/or the proximal portion of the cutting tool 125 may be formed relatively thicker than other portions thereof.

Figure 15:
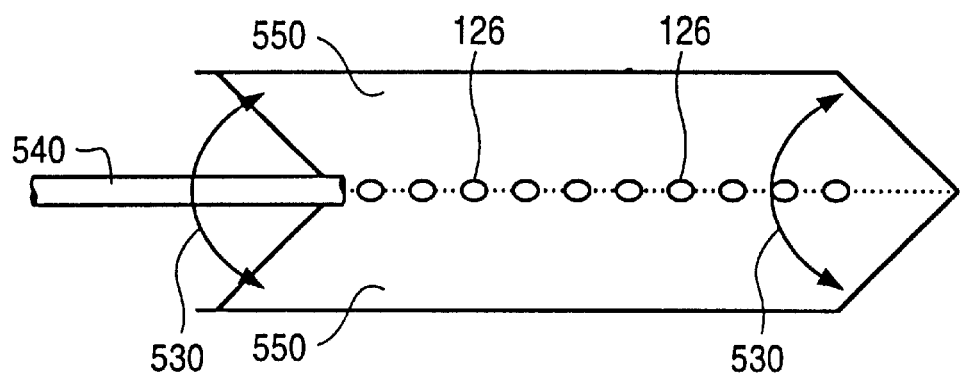
FIG. 15 shows an embodiment of a cutting tool according to another embodiment of the present invention, in an intermediate state of manufacture.
Figure 16:
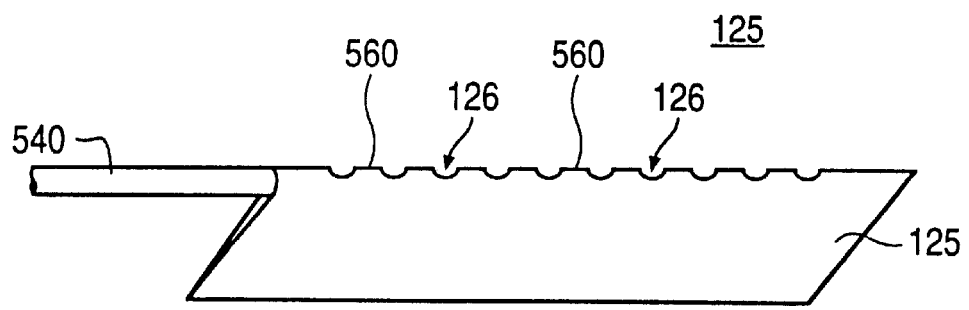
FIG. 16 shows the cutting tool of FIG. 15, bent in its final configuration.

Another embodiment of the cutting tool 125 is shown in FIGS. 15 and 16. As shown therein, the cutting tool 125 may be formed by a thin sheet of steel or shape memory alloy. The sheet may include a plurality of through holes 126 to allow the anaesthetic or other fluid to be instilled therethrough. A small tube 540 may be disposed on the sheet, aligned with the through holes 126. The sheet may be folded in the direction indicated by the arrows 530, thus securing the tube 540 between the two folded sides of the sheet. The edges 550 of the sheet may be sealed together to render them fluid tight. For example, the sides 550 of the sheet may be welded together or secured by other means known to those of skill in the metal working arts. The edges 560 between the through holes 126 may be sharpened, to allow the cutting tool 125 to efficiently cut through soft tissue. As shown in FIG. 16, the tube 540 may deliver anaesthetic or other fluid to the cutting tool 125, which delivers minute amounts thereof precisely where it is needed: where the cutting edges 560 of the cutting tool 125, thereby affording the patient immediate relief and minimizing the amount of anaesthetic that need be delivered. The proximal end of the tube 540 may be in fluid communication with an anaesthetic reservoir (not shown) and/or an anaesthetic pump (also not shown).

Figure 6:
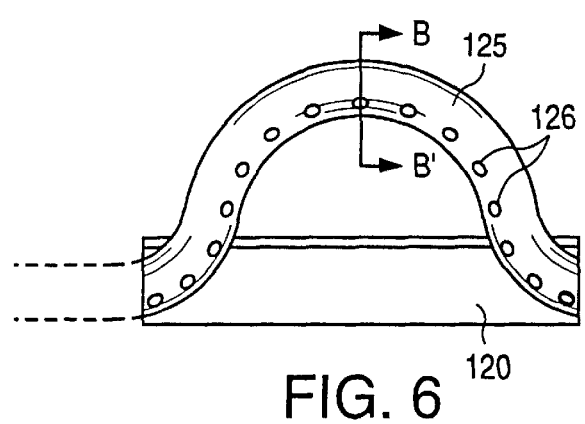
FIG. 6 shows a detailed view of another cutting tool suitable for use with the excisional device according to the present invention.
Figure 7:
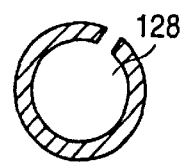
FIG. 7 shows a cross section of the cutting tool, taken along line BB' in FIG. 6.

Alternatively, the cutting tool 125 may include a thin wire, such as shown at 125 in FIGS. 6 and 7. In this case, an external radio frequency (hereafter, RF) power source 240 (shown at 240 in FIG. 2C) supplies the cutting tool 125 with RF energy via two bipolar electrodes (not shown) attached to the cutting tool 125 of FIG. 6. Other energy sources may also be used within the context of the present invention, RF power being discussed herein for illustrative purposes only. The RF power delivered by the RF power source 240 allows the cutting tool 125 of FIG. 6 to become an electrosurgical cutting and/or an electrocoagulating tool by selectively varying the power applied to the cutting tool 125. Suitable generators for such an electrosurgical cutting device 125 are known to those of skill in this art. An example of such a suitable generator is described in U.S. Pat. No. 4,903,696 issued Feb. 27, 1990 and assigned to Everest Medical Corporation, Brooklyn Center, Minn., the disclosure of which is incorporated herewith in its entirety. As with the cutting tool 125 shown in FIGS. 4 and 5, the cutting tool 125 of FIGS. 6 and 7 includes an internal lumen 128 and a plurality of through holes 126 to allow anaesthetic or other fluid to be delivered to the surrounding tissue as the cutting tool 125 cuts through the soft tissue as the device 100 is rotated.

As alluded to above, the excisional biopsy device 100 according to the present invention cuts out a (not necessarily symmetrical) volume of revolution as it cuts through the soft tissue upon rotation of the generally tubular member 110. This severed mass of tissue may be stabilized using an extendable tissue anchoring device, which anchoring device also assists in the retrieval of the severed tissue sample from the breast. The anchoring device may, for example, include a suction device or other substantially rigid anchor member to anchor the tissue sample. Alternatively, the severed tissue sample may be collected in a tissue collection device, as shown at reference numeral 260 in FIGS. 2A and 2B. The tissue collection device 260 is attached externally to the tubular member 110, and preferably also to the trailing edge of the cutting tool 125. The tissue collection device 260 is preferably formed of a thin and flexible plastic membrane shaped like a bag. The opening of the bag-shaped collection device 260 is preferably co-extensive with the opening 120 and is preferably attached to the tubular member 110 and to the trailing edge of the cutting tool 125. In this manner, the opening or "mouth" of the bag-shaped collection device 260 opens and closes along with the bowing and retraction, respectively, of the cutting tool 125. Indeed, the "mouth" of the bag-shaped collection device 260 is opened when the cutting tool 125 is bowed and extended out of the cutter window 120 and substantially closed when the same is retracted within the cutter window 120, as the two edges (one attached to the tubular member 110 just adjacent to the edge of the cutter window 120 and the other attached to the trailing edge of the cutting tool 125) of the collection device are then pressed together.

Therefore, when the excisional device 100 is inserted into soft tissue and rotated, the cutting tool 125 may be caused to bow and to extend outwardly from the cutter window 120 and caused to cut tissue coming into contact therewith. As the device 100 rotates and cuts, the tissue between the cutting tool 125 and the tubular member 110 tends to advance toward and into the collection device. As the cutting tool 125 is in its bowed and extended state, the "mouth" or opening of the bag-shaped collection device 260 is also correspondingly open, allowing the severed tissue to collect therein. As the revolution of the tubular member 100 is completed, the cutting tool 125 may be retracted and caused to assume a configuration wherein it is disposed within the recessed cutter window 120, substantially flush with the outer surface of the tubular member 110, as shown in FIG. 2B. In this configuration, the collection device 260 is closed, thereby securing the excised tissue sample therein. The device 100 may then be safely retracted from the main tissue mass, such as the breast. As the excised sample is physically isolated from the remaining tissue mass, the probability of seeding the surrounding tissue with potentially abnormal cells is markedly decreased. This probability is also further decreased, as the excisional device 100 according to the present invention allows the surgeon to obtain adequate margins of healthy tissue surrounding the target lesion by choosing the degree of bowing and extension of the cutting tool 125. In this manner, the integrity of the lesion itself is not violated, thereby maintaining tissue architecture intact.

As the collection device 260 is preferably formed of a thin and flexible membrane, it is able to lay substantially flat against the outer surface of the tubular member 110 or slightly recessed within the cutter window 120 during insertion thereof into the soft tissue. The collection device 260, therefore, offers little additional drag and resistance to the device 100 as it is inserted into the incision made in the patient's skin during or prior to the procedure. Suitable materials for the tissue collection device 260 include plastics and nylon, for example. Any strong adhesive may be utilized to secure the tissue collection device 260 to the tubular member 110 and to the cutting tool 125. Other means of securing the collection device 260 may also be employed without, however, departing from the scope of the present invention. Likewise, the tissue collection device 260 may be formed of a material other than specifically enumerated herein while remaining within the spirit of the present invention. Preferably, the shape and size of the tissue collection device 260 are such as to minimize drag on the excisional biopsy device 100 as it is inserted and rotated into the tissue. For example, the tissue collection device 260 preferably should be only as large as necessary to contain the excised tissue sample.

The excisional biopsy device 100 according to the present invention is preferably accurately positioned adjacent to the lesion within the breast or other organ. Toward that end, the present invention allows the surgeon to gain near real time or real time information as to the internal structure of the soft tissue during the procedure itself. Referring now back to FIGS. 1 and 2C, the present invention may include a transducer 270 mounted within the distal portion of the tubular member 110. This transducer 270 is preferably adapted to image tissue about to be cut by the cutting tool 125 as the excisional biopsy device 100 is rotated within the soft tissue. Indeed, the transducer 270 preferably generates information relative to the tissue about to be cut—that is, tissue that that has not yet been brought into contact with the cutting tool 125 as the tubular member 110 rotates about its longitudinal axis. In this manner, as the rotational speed of the excisional biopsy device 100 is preferably quite slow (the rotation may be manually carried out or may be caused by a slow moving motorized unit attached to the tubular member 110), the surgeon may evaluate the information generated by the transducer 270 and may, based upon this information, vary the degree of bowing and extension of the cutting tool 125. For example, when the device 100 is positioned adjacent to the lesion of interest and rotated, the transducer 270 will detect the presence and location of the lesion before the lesion comes into contact with the cutting tool 125. After the lesion has been detected by the transducer 270, the surgeon may push on the push or turn knob 226 or other structure that causes the cutting tool to bow and extend from the cutter window 120. The lesion (and preferably an adequate margin of healthy tissue) will then be severed from the main mass, and optionally collected, for example, in the tissue collection device 260. When the transducer 270 indicates that the rotation of the tubular member has brought the cutting tool 125 past the lesion, the cutting tool 125 may be retracted within the cutter window 120. The cutting, it can be seen, may be specifically tailored to the size and shape of the lesion within the main tissue mass in near real time or in real time, thereby allowing the surgeon to excise all of the tissue required and only the tissue that is necessary to achieve the intended results.

Preferably, the transducer 270 is an ultrasound sensor mounted substantially flush with the external surface of the tubular member 110. The ultrasound sensor 270 is preferably electrically connected, via a communication channel such as electrical conductors, to at least one data processing and display device, shown at reference 250 in FIG. 2C. The data processing and display device(s) 250 allows the surgeon to see, in near real time or in real time, the internal structure of the tissue about to be cut by the cutting tool 125. This allows the surgeon not only to see a graphical representation of the internal structure of the tissue during the procedure itself, but also allows the surgeon to assure himself or herself that the entire lesion or group of lesions has been properly excised by, for example, rotating the tubular device within the tissue while the cutting tool is retracted within the cutter window 120 while the transducer 270 is energized. Viewed from another aspect, therefore, the present invention is an intra-tissue ultrasound imaging device that may, but need not include a cutting tool, such as referenced by numeral 125 in the figures.

In operation, the (e.g., ultrasound) transducer sweeps a plane (graphically shown at 280 in FIG. 3A) within the tissue ahead of the work element, such as cutting tool 125. In selecting the operational characteristics of the ultrasound transducer 270, the surgeon must balance the required resolution (i.e., the smallest feature that must be discernable) with the degree of penetration of the ultrasound waves within the tissue and the intensity of the ultrasonic waves generated. In general, higher frequencies allow better resolution. However, high frequencies do not penetrate the tissue as far as do lower frequency ultrasound waves. Preferably, the ultrasound transducer 270 is tuned within the range from about 5 MHz to about 20 MHz. More preferably, the ultrasound transducer 270 is tuned within the range of about 7.5 MHz to about 20 MHz. For example, in the case wherein the excisional biopsy device 100 according to the present invention is used within the female breast, the ultrasound transducer may be tuned within the range of about 10 MHz to about 13 MHz.

Figure 9:
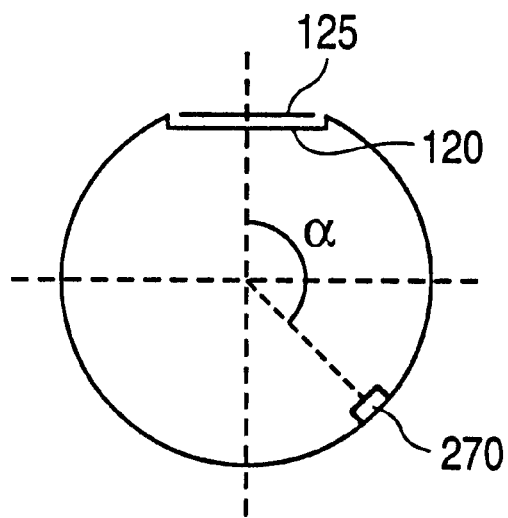
FIG. 9 is a cross-sectional schematic of the tubular member 110, to illustrate the relative placements of the cutter window 120 and of the transducer 270 about the circumference of the tubular member 110. Unnecessary details have been omitted for clarity.

To effectively image the internal tissue structure prior to cutting it with, for example, the cutting tool 125, the transducer 270 must be positioned within the tubular member 110 away from the cutting tool 125. With reference to FIG. 9, the transducer 270 may be disposed within the tubular member at an angle $\alpha$ relative to the cutting tool 125. The angle $\alpha$ is preferably no smaller than that necessary to effectively control the operation of the work element (such as cutting element 125) in response to information gathered from the transducer 125 as the tubular member 110 rotates. This angle $\alpha$, therefore, is dependent at least upon the rotational speed imposed upon the tubular member 110 and upon the time necessary for the surgeon to assimilate the information generated by the transducer and to effectively control the cutting tool 125 in response to such information. Preferably, the angle a is less than about 180 degrees.

When used in conjunction with an intra-tissue ultrasound transducer, such as shown at 270, the excisional biopsy device 100 according to the present invention may include a variety of work elements in place of or in addition to the cutting tool 125. Such work elements include, for example, an abrasive device, a reciprocating cutting device, an electrosurgical device or a vibrating device.

In the case of lesions within the breast, it is useful to stabilize the breast prior to imaging and performing invasive procedures. Such stabilization is conventionally performed by compression plates that squeeze the breast and compress the tissue therein. Such compression is necessary to allow x-ray radiation, as used in mammography, to produce a useful image. Although such compression is not needed or believed to be desirable according to the present invention, stabilization of the breast remains necessary. For this purpose, the breast stabilization device described in commonly assigned U.S. patent application Ser. No. 09/158,215, filed Sep. 22, 1998, the disclosure of which is incorporated herein in its entirety, may be useful.

Figure 3A:
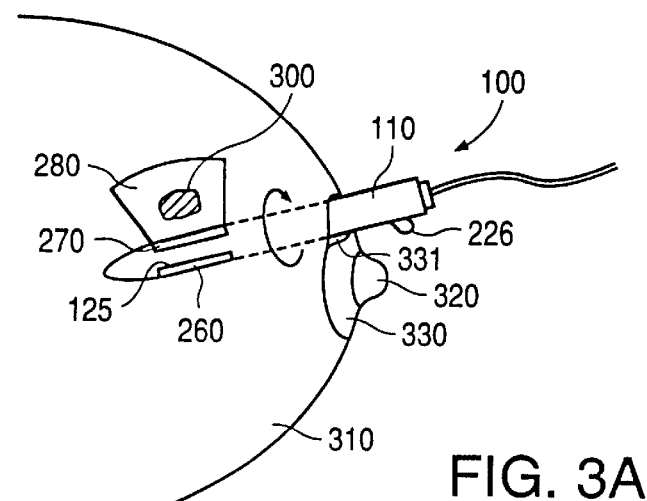
FIG. 3A depicts the operation of an embodiment of the excisional device and method according to the present invention.
Figure 3B:
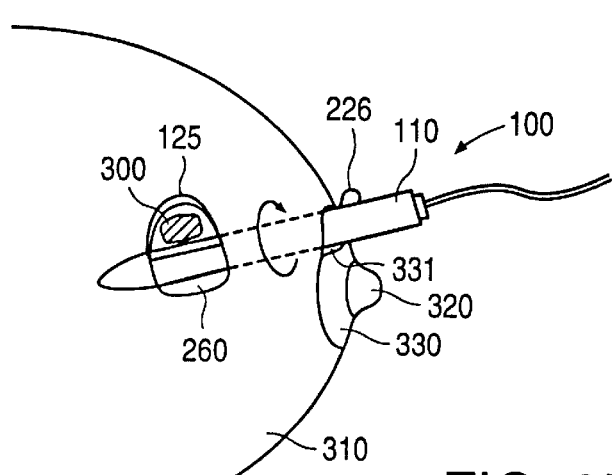
FIG. 3B further shows the operation of an embodiment of the excisional device and method according to the present invention.
Figure 3C:
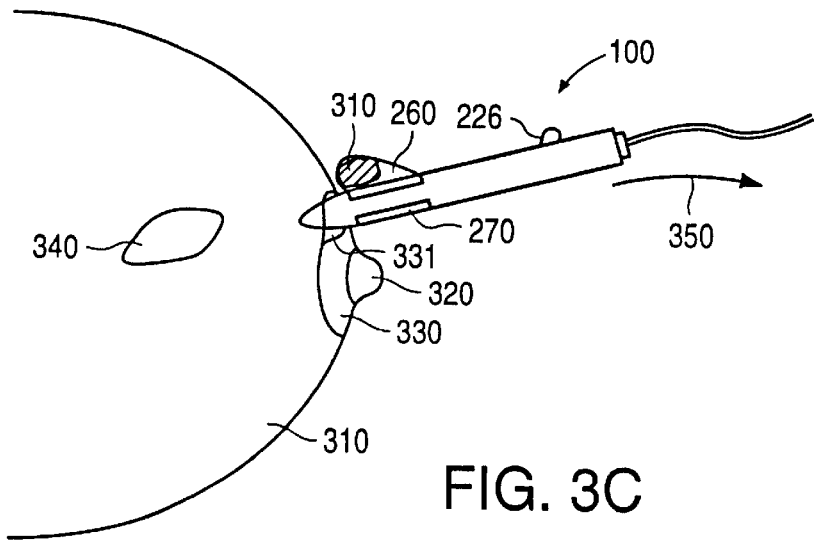
FIG. 3C further depicts the operation of an embodiment of the excisional device and method according to the present invention.

Reference is now made to FIGS. 3A, 3B and 3C, which illustrate an embodiment of the excisional biopsy method according to the present invention. Although FIGS. 3A–3C illustrate an embodiment of the present invention within the context of breast surgery, it is to be understood that the present inventive method is equally applicable to other soft tissue masses, such as, for example, lung, thyroid or liver tissue, with only minor modifications which will become apparent to skilled practitioners in this art.

Turning first to FIG. 3A, a small incision 331 is made in the breast 310, preferably in the peri-areolar region. Preferably, the breast is stabilized, using, for example, the breast stabilizing device disclosed in U.S. patent application Ser. No. 09/158,215, referred to above. The portion of the device 100 that remains outside of the soft tissue may include attachment means (not shown) for clamping the device to a rim structure, for example, to allow stable operation and precise guidance thereof. The small incision is preferably made on the border of the areola 330 surrounding the nipple 320, as this provides a better cosmetic scar than on the skin on the side of the breast 310. Depending on the size of the lesion and the size of the excisional biopsy device 100 to be inserted therein, an expandable sheath (an example of which is shown at reference numeral 495 in FIG. 13) may be inserted into the breast tissue. In any event, the excisional biopsy device 100 is inserted into the breast tissue and positioned adjacent the lesion 300, which may be, for example, a microcalcification or other abnormal lesion. Once in position, the device 100 is rotated, for example, in the direction indicated in FIG. 3A. The portion of the excisional biopsy device 100 that remains outside the soft tissue may have a greater diameter than the portion thereof that is designed to penetrate the soft tissue. This aids in manual rotation of the device 100. In the configuration depicted in FIG. 3A, the cutting tool 125 is retracted within the cutter window 120 and the tissue collection device 260, if present, is substantially flat against the external surface of the tubular member 110. The device 110 is rotated about its longitudinal axis and the transducer 270 is energized, the information therefrom being transmitted to, for example, the display device 250 shown in FIG. 2C. When the lesion 300 comes into view, the surgeon then gauges the size, shape and location thereof and controls the bowing and extension of the work element, such as cutting tool 125 based on the information received from the transducer 270 and displayed upon the display 250. FIG. 3B depicts the situation wherein the lesion 300 has been imaged and the surgeon has extended the cutting tool 125 to sever the lesion 300 from the surrounding breast tissue. The severed tissue may be received and collected in a tissue collection device 260, as the device 100 rotates. Anaesthetic and/or antibiotic (or other) fluids may be delivered directly to the affected tissue by through holes 126 (best seen in FIGS. 2A, 2B and FIGS. 4–7), greatly decreasing pain during the procedure After the lesion and any desired margin of healthy tissue is severed from the main breast tissue mass, the cutting tool 125 is retracted within the cutter window 120. This closes the tissue collection device 260, if present, and allows the entire device 100 to be retracted from the breast in the direction of arrow 350, as shown in FIG. 3C. If the tissue collection device 260 is present, the lesion 300 will be isolated from surrounding tissue by the membrane of the tissue collection device 260, thus minimizing any possibility of seeding potentially abnormal cells to surrounding breast tissue. Moreover, the tissue architecture of the retrieved lesion 300 is substantially preserved, thereby allowing accurate histopathology to be performed upon the entire mass excised from the breast. Indeed, any compression such tissue may undergo is believed to be solely due to the retraction of the device back through the entrance track of the device 100 in the uncompressed breast tissue. Thereafter, when the excisional device 100 is removed from the breast 310, the push or turn knob 226 may be acted upon to extend and bow the cutting tool 125, thereby allowing the excised lesion to be retrieved from the tissue collection device 260 for examination. If the tissue collection device is not present, conventional suction means may be employed to extract the severed lesion from the surrounding breast tissue. Bleeding is controlled by suitably varying the RF or other power source applied to the electrosurgical cutting tool 125, if present, to stem the bleeding by cauterizing the tissue coagulating the blood.

After the procedure, a small cavity remains in the breast where the lesion had previously been. However, since no compression of the breast was carried out, no expansion of the tissue occurs after the procedure, unlike conventional techniques. Therefore, the cavity and the entrance and exit path of the device remain as small as possible, leading to fewer complications, less tissue trauma and improved aesthetics.

According to another embodiment of the present invention, shown in FIGS. 10, 11 and 12, the transducer 270 is replaced by a removable transducer core 400. The removable transducer core 400 includes an active element 440 configured to perform intra-tissue imaging and of relaying information back to a display device (shown in FIG. 14) via a communication channel, such as shown at reference numeral 460. The communication channel 460 may be wireless or may include, for example, optical fibers and/or electrical conductors. The active element 440 may draw power from an internal battery (not shown) or from a power source, such as shown at reference numeral 480. The active element 440 may include an ultrasound transducer. Other types of transducers may be used instead of or in addition to an ultrasound transducer. The removable transducer core 400 preferably includes a generally tubular shaft 430. A proximal section 450 is included near the proximal portion of the transducer core 400.

To accommodate the removable transducer core 400, the excisional device 100 of FIG. 10 includes an internal lumen 420 through which the removable transducer core 400 may be inserted. Preferably, the excisional device 100 is used once and disposed of, for safety and functional reasons. The removable transducer core 400, however, may either be disposable or re-usable for a limited number of uses. To allow the active element 440 of the transducer core 400 to image the lesion to be excised and the surrounding tissue, the generally tubular member 110 of the excisional device 100 includes a transducer window 410. When the removable transducer core 400 is inserted within the internal lumen 420, the proximal section 450 of the core 400 preferably snaps into a locked configuration with the proximal end of the excisional device 100. When in its locked configuration, the active element 440 of the transducer core 400 is aligned with and faces the transducer window 410, to allow the active element 440 to image the lesion and the surrounding tissue therethrough.

FIG. 11 shows an embodiment of the removable core 400 according to the present invention. As the removable core 400 may advantageously be used independently of the excisional device 100, the removable core 400 includes a distal tapered tip 470, to allow it to easily penetrate soft tissue. Moreover, its thin profile allows the surgeon to insert the removable core 400 within soft tissue without, however, unduly damaging the tissue or making a large incision. The removable core 400 allows the surgeon to precisely localize the lesion to be excised from within the tissue itself. For example, the active element 440 of the removable core 400 may include an ultrasound transducer having similar characteristics as the sensor 270, and may be used alone or in addition to surface ultrasound to localize the lesion with a great degree of precision.

FIG. 12 shows a cross section of the embodiment of the excisional device 100 of FIG. 10, taken along line AA'. As shown in FIG. 12, the cutting tool 125 is exposed through the transducer window 120. The window 120 may, as shown in FIG. 12, include support guides 122 to support and guide the cutting tool 125 as it is outwardly extended and bowed. The tissue collection device 260, for clarity, is not shown in either FIG. 10 or 12. However, to accommodate the bulk of the excised tissue sample collected in the tissue collection device 260 after the cutting and collecting operation described herein, the tubular member 110 may include a recessed section 131. The recessed section provides space for the collected (e.g., bagged) tissue sample in the tissue collection device 260 when the excisional device is removed from the soft tissue mass. In this manner, the collected tissue sample within the tissue collection device 260 does not protrude from the generally smooth outer surface of the excisional device 100 upon retraction of the latter from the soft tissue mass from which the tissue sample is excised. The internal lumen 420 allows the removable core 400 to slide therein and to properly position the active element 440 facing the transducer window 410.

Figure 13:
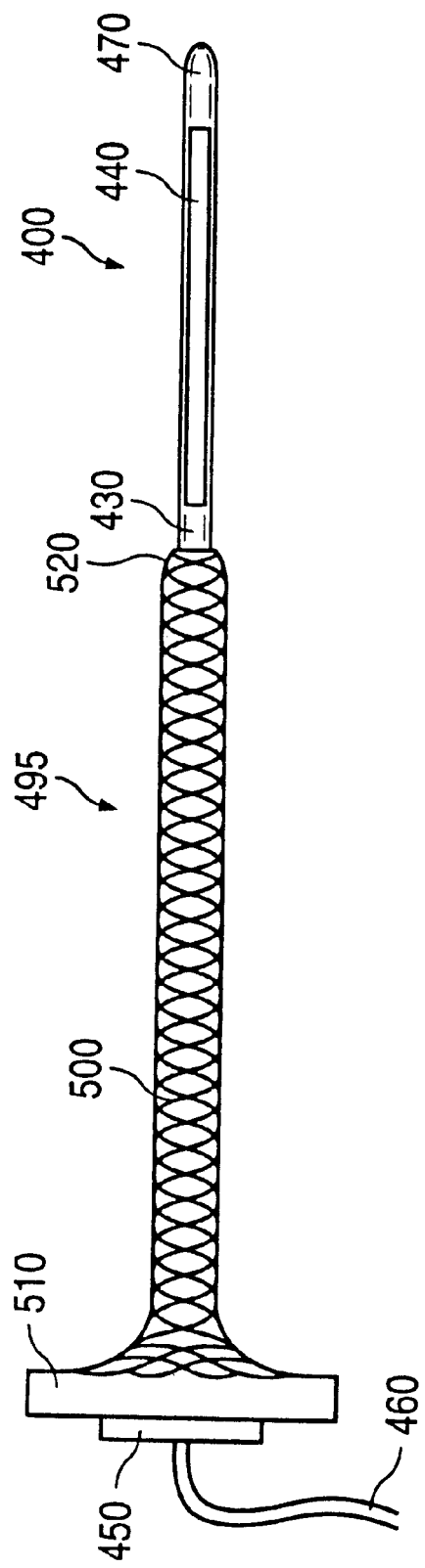
FIG. 13 shows an expandable sheath according to an embodiment of the present invention.

FIG. 13 shows the removable core 400 inserted within an expandable sheath 495. The expandable sheath includes a proximal base section 510. Attached to the proximal base section 510 is a generally cylindrical expandable meshwork 500 of, for example, plastic or nylon fibers. The meshwork 500 may be somewhat tapered at its distal end 520, to provide a smooth transition between the expandable meshwork 500 and the removable core device 400. The proximal section 450 of the core 400 may snap-fit to the proximal base section 510 of the expandable sheath 495, so as to be securely and removably attached thereto. As shown in FIG. 13, the expandable meshwork 500 expands just enough to accommodate the removable core 400 inserted therein. In practice, the expandable sheath 495 and removable core 400 assembly may be inserted within the soft tissue together, to allow the surgeon to image the lesion prior to inserting the somewhat greater diameter excisional device 100 therein. Thereafter, the surgeon may retract the removable core 400 from the expandable sheath 495, leaving the expandable sheath 495 in place within the soft tissue, such as the breast.

Figure 14:
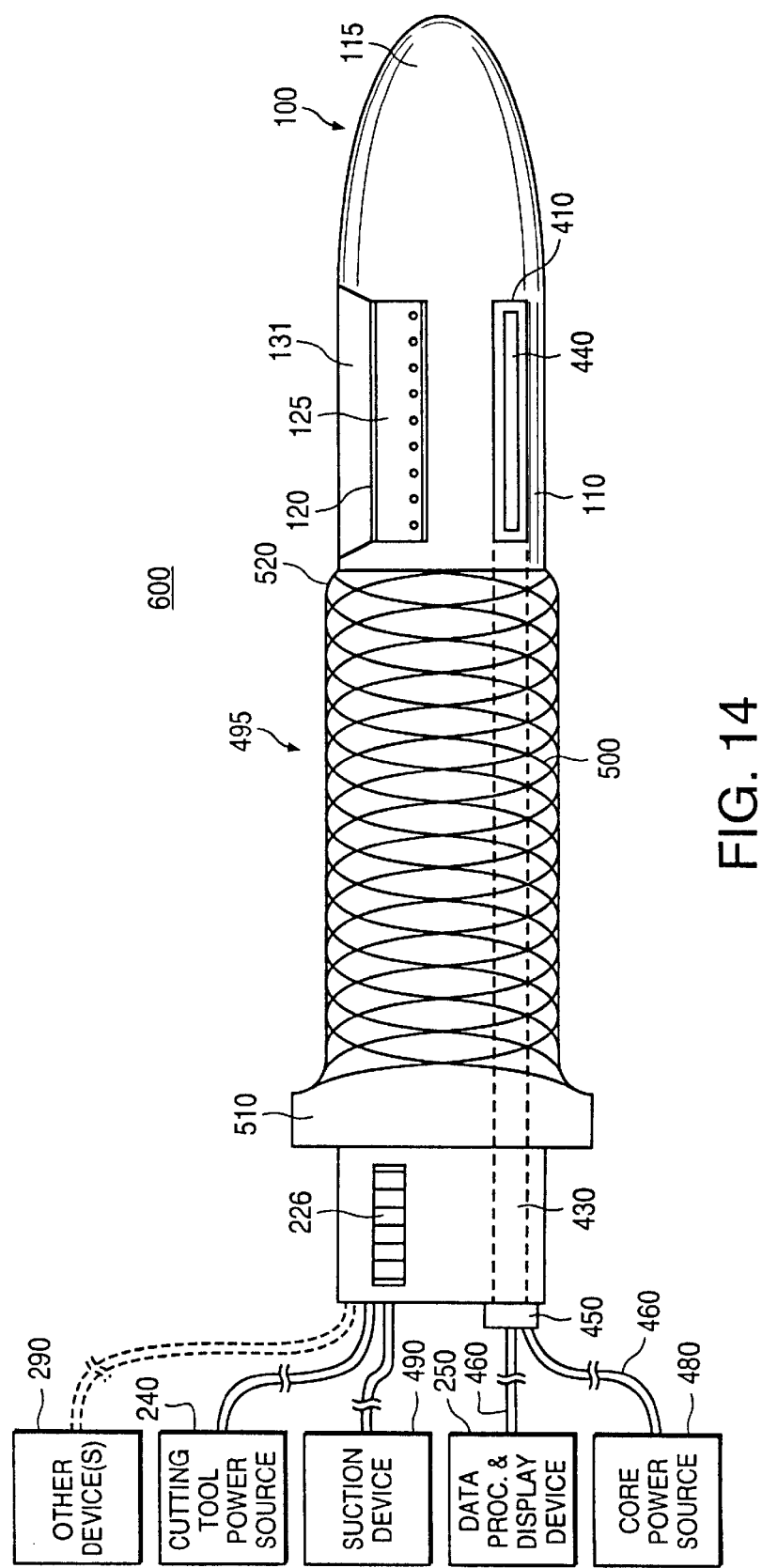
FIG. 14 shows another embodiment of a soft tissue excisional device assembly according to the present invention.

FIG. 14 shows another embodiment of a soft tissue excisional device assembly 600 according to the present invention. In the configuration shown in FIG. 14, the removable core 400 is inserted and secured within the excisional device 100 so that the active element 440 faces out of the transducer window 410. As in FIG. 10, the tissue collection device 260 is not shown, for clarity. In FIG. 14, the excisional device 100 is shown inserted within the expandable sheath 495. Indeed, the excisional device 100, in FIG. 14, is shown inserted within and past the distal end 520 of the meshwork 500, so the distal portion of the excisional device 100 including the cutting tool 125 and the transducer window 410 extends therethrough. The meshwork 500, in FIG. 14, has expanded to accommodate the diameter of the excisional device 100. The proximal portion of the excisional device 100 may extend from the proximal base section of the expandable sheath 495. This allows the push or turn knob 226 (a turn knob 226 shown in FIG. 14) to be manually accessible to the surgeon. A number of peripheral devices may be connected to the assembly 600. Examples of such include a core power source 480, which may be, for example, an electrical source for an ultrasound transducer, one or more data processing and display devices 250 on which the internal structure of the tissue imaged by the active element 440 of the core 400 may be displayed, suction means 490, a cutting tool power source (a variable RF energy source, for example), and/or other devices 590. The suction device 490 may provide a suction force to the window 120 through an internal lumen to facilitate cutting of the tissue by the cutting tool 125.

The excisional device assembly 600 may be rotated in toto, or the excisional device 100 may be rotated independently of the expandable sheath 495, depending upon the degree of friction between the two. Preferably, the excisional device 100 is removable from the expanded sheath 495 shown in FIG. 14, while leaving the expanded sheath 495 in place within the soft tissue. In this manner, after retraction of the excisional device 100 from the sheath 495, the sheath 495 remains in place within the soft tissue to allow other instruments to be inserted therethrough. For example, the removable core 400 may, after the excisional procedure proper, be re-inserted through the expanded sheath 495 to the excision site. Thereafter, the surgeon may cause the active element 440 of the removable core 400 to become energized, to image the excision site to insure that the complete lesion has been removed from the soft tissue mass. To do this, the surgeon may rotate the removable core 400 within the expanded sheath 495 while observing the display or displays for signs of the lesion. If none is found, it is probable that the entire lesion has been successfully removed and the surgeon may then retract the core 400 from the sheath 495 and the sheath from the tissue mass and repair the incision made prior to inserting the assembly therein. Alternatively, the surgeon may choose to remove both the expanded sheath 495 and the core 400 simultaneously.

Figure 17:
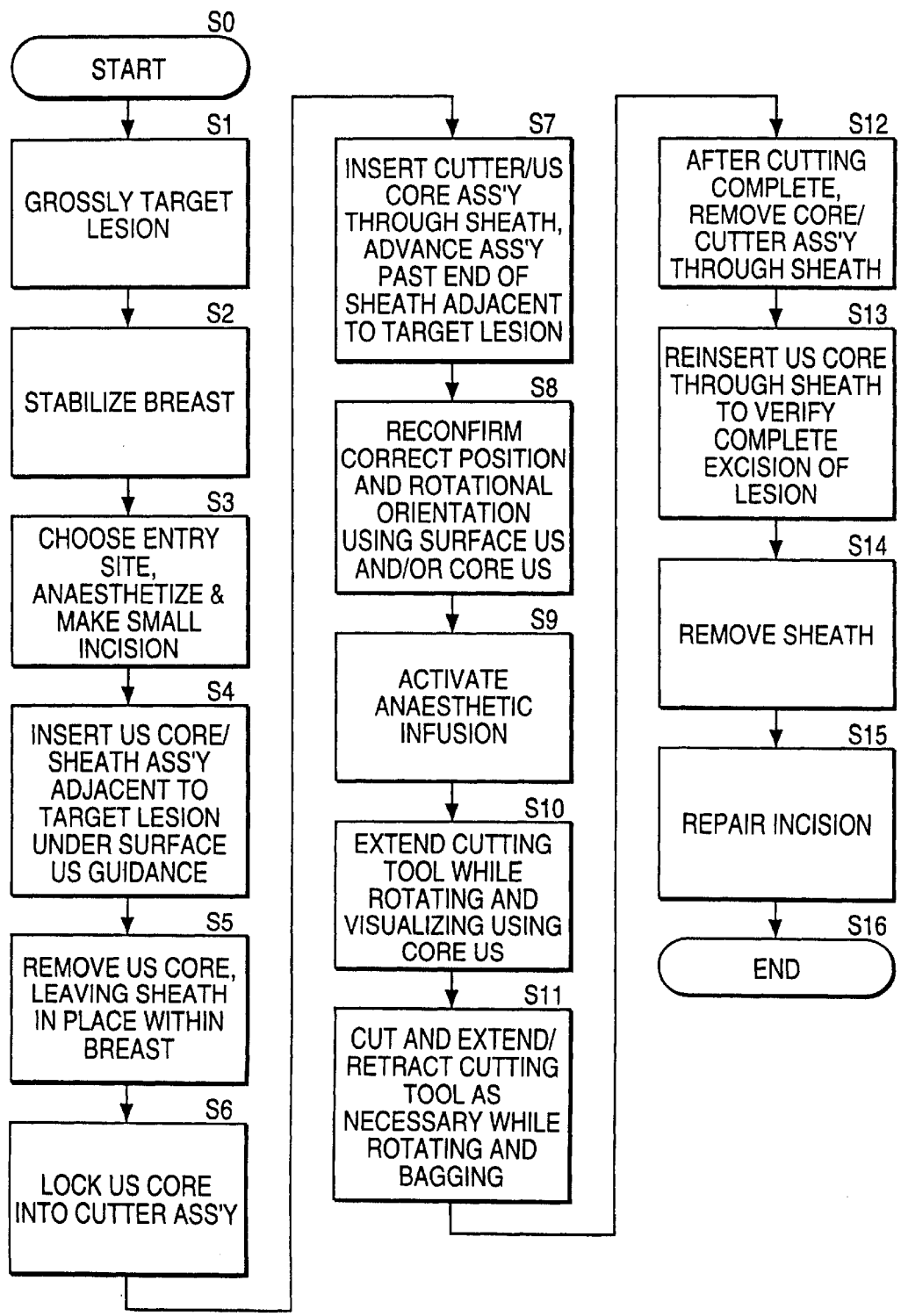
FIG. 17 shows an embodiment of the method of excisional biopsy method according to the present invention.

FIG. 17 shows an embodiment of the method of excisional biopsy method according to the present invention. In FIG. 17, it is assumed that the soft tissue from which the lesion is to be excised is breast tissue and that the active element 440 of the removable core 400 is an ultrasound transducer. Other combinations are possible, and the present invention should not be limited to applications related to breast tissue and ultrasound. The removable core 400 and the active element 440, in FIG. 17, are together abbreviated as "US CORE", a shorthand expression for the phrase "ultrasound core" and the word "assembly" is abbreviated to "Ass'y". Moreover, it is to be understood that the steps shown in FIG. 17 constitute but a broad outline of one possible embodiment of the present inventive method. Therefore, other additional steps may be inserted between the steps shown in FIG. 17, or other steps may be substituted for some of the displayed steps without, however, departing from the scope of the present invention.

The method starts at step S0. In step S1, the lesion within the breast is grossly targeted, using, for example, standard or stereotactic surface ultrasound. In step S1, a rough estimate of the location of the lesion within the breast is obtained. The surgeon, after having located the general location of the lesion, may mark the location thereof on the ultrasound display or displays and/or on the corresponding surface of the breast, with an "X", for example. The breast is stabilized in step S2. Preferably, the breast is stabilized in an uncompressed or slightly expanded state, in the manner disclosed in the commonly assigned and co-pending U.S. patent application Ser. No. 09/158,215 previously discussed and incorporated by reference herein. The woman's other breast is preferably placed within a counterpart breast stabilizing device, which helps to immobilize the woman during the procedure. One of the ultrasound ports of the breast stabilizing device is aligned with the lesion, for example, by aligning one of its ultrasound ports with the marked location on the breast. Suction is then applied to the breast stabilizing device, in the manner described in the above-referenced application and a correctly oriented surface ultrasound device is secured to the ultrasound port of the stabilizing device. Other means of stabilizing the breast may also be used without, however, departing form the present invention.

In step S3, an entry site on the breast is chosen. Preferably, the peri-areolar region is chosen as the incision site, as scars within the peri-areolar region are less visible than scars in more exposed regions of the breast and for other anatomical reasons. The incision site is then anaesthetized, both on the skin surface and subcutaneously. Also in step S3, a small incision is made at the chosen incision site. Preferably, the incision is large enough to accommodate the expandable sheath 495 with the removable core 400 inserted therein. In step S4, the expandable sheath 495, together with the removable core inserted therethrough, is inserted into the incision made in step S3. Under surface ultrasound guidance, for example, the sheath 495/core 400 assembly is navigated adjacent to the lesion. If the sheath 495/core 400 assembly can be properly positioned adjacent to the target lesion, the method according to the present invention proceeds to step S5. If the sheath 495/core 400 assembly cannot be properly positioned adjacent to the target lesion, all or a portion of the above-detailed steps are repeated until proper positioning of the sheath 495/core 400 assembly is achieved, adjacent to the target lesion.

Assuming now that step S4 has been completed to the surgeon's satisfaction, the core 400 is removed from the expandable sheath 495 and the expandable sheath 495 is left in place within the breast, as shown in step S5. In step S6, the removable core 400 is inserted within the internal lumen 420 of the tubular member of the excisional device 100 and locked securely in place, so that the active element 440 (in this case, an ultrasound transducer) is aligned with and faces out of the transducer window 410 of the device 100. Again leaving the expandable sheath 495 in place within the breast, the excisional device 100 (with the core 400 secured therein) is advanced through the expandable sheath 495. The sheath 495 then expands within the breast tissue to accommodate the somewhat larger diameter of the excisional device 100. The excisional device 100 is advanced past the tapered distal end 520 of the sheath 495, so the assembly including the sheath 495, the excisional device 100 and the removable core 400 is positioned adjacent to the target lesion within the breast tissue, as shown in step S7.

In step S8, the correct position adjacent the target lesion and the correct rotational orientation of the aforementioned assembly (FIG. 14) is confirmed, using surface ultrasound and/or the core ultrasound 400. The active element 440 of the core 400 is particularly well suited for this task, as the excisional device 100 may be rotated within the tissue, and positioned so the cutting tool 125 is properly positioned to allow it to rotate, extend and bow outwardly in such a manner as to precisely sever the lesion from the surrounding tissue with an adequate margin of healthy tissue. Indeed, the ultrasound transducer 440, as it rotates along with the excisional device 100, images the lesion before the cutting tool 125 cuts it, thereby allowing the surgeon to optimally deploy the cutting tool based upon his or her observation of the imaged tissue on a display or displays. In step 9, the surgeon may activate an anaesthetic infusion, the anaesthetic being delivered by the cutting tool 125 via the plurality of through holes 126, best seen in FIGS. 4 and 6. Step S9 may be skipped if the cutting tool 125 does not provide for through holes 126 or if the surgeon does not deem it necessary to anaesthetize the tissue during the rotation of the cutting tool 125. For example, the tissue may have been previously anaesthetized. While rotating at least the excisional device 100 (with the removable core 400 secured therein), the cutting tool 125 is extended using, for example the push or turn knob 226 shown in FIGS. 2C and 14, thereby causing the cutting tool 125 to extend from the window 410 and to bow outwardly, as shown in step S10. Depending on the amount of friction between the excisional device 100 and the expandable sheath 495 (which may be freely chosen depending upon the choice of material for the meshwork 500 and the configuration of the mesh), the sheath 495 may rotated along with the excisional device 100. The degree of extension and bowing may be finely controlled by the surgeon as the excisional device 100 is rotated, either manually or by a motorized unit (not shown) coupled thereto. As the cutting tool is rotated, the severed tissue sample is preferably collected (e.g., bagged) in a tissue collection device 260 (FIGS. 2A and 2B), as shown at step S11. The blood vessels may be coagulated as the cutting tools rotates and cuts the tissue, or afterwards. In step S12, after the excisional device 100 has completed at least one revolution within the breast and has cut a volume of revolution therein, including at least the target lesion and preferably a margin of healthy tissue surrounding the lesion, the excisional biopsy device 100 and removable core 400 assembly are retracted through the sheath 495, leaving the sheath 495 once again in place within the breast. Preferably, the tissue collection device 260 and the tissue sample it encloses lie within the recessed section 131 of the generally tubular member 110. In this manner, the filled collection device 260 does not protrude or protrude too much from the surface of the tubular member 110, thereby allowing the retrieved tissue sample to be readily retracted with the excisional device 100 through the sheath 495.

After retraction of the excisional device 100, the core 400 may be retracted from the device 100 and re-inserted through the sheath 495 left in place within the breast. The core 400 is then advanced adjacent to the excision site, and rotated to allow the surgeon to image the excision site to insure that the entire lesion has indeed been removed, as shown in step S13. Some or all of the above steps may be repeated should the imaging of the excision site by the core 400 within the sheath 495 reveal that a portion of the target lesion was not excised. Assuming that all of the target lesion has been removed, the incision is repaired by, for example, suturing the peri-areolar incision site. The method ends at step S16.

While the foregoing detailed description has described several embodiments of this invention, it is to be understood that the above description is illustrative only and not limiting of the disclosed invention. For example, the shape of the cutting tool 125 may differ from that shown in the Figures. Other transducers and/or work elements may be added or substituted for those shown and described herein. For example, a piezoelectric transducer may be advantageously utilized to vibrate the cutting tool 125 at high frequencies. A number of other modifications will no doubt occur to persons of skill in this art. All such modifications, however, should be deemed to fall within the scope of the present invention. Thus, the invention is to be limited only by the claims as set forth below.

What is claimed is:

1. An excisional biopsy method for soft tissue, comprising the steps of:

inserting a generally tubular member into the tissue, the tubular member including a cutting tool adapted to selectively bow away from the tubular member and an external tissue collection device near a distal tip of the tubular member;

rotating the tubular member;

selectively varying a degree of bowing of the cutting tool;

collecting tissue severed by the cutting tool in the tissue collection device; and retracting the tubular member from the soft tissue.

2. The method of claim 1, wherein the rotating step is carried out by manually rotating the tubular member.

3. The method of claim 1, wherein the tubular member further includes an imaging transducer and wherein the method further comprises the steps of:

displaying information received from the transducer on a display device; and varying the degree of bowing of the cutting tool based upon the displayed information from the imaging transducer.

4. The method of claim 3, wherein the cutting tool comprises an electrosurgical blade and wherein the method further comprises the step of varying a power applied to the electrosurgical blade based upon information received from the transducer.

5. The method of claim 1, further comprising the step of stabilizing the soft tissue in an uncompressed state prior to the inserting step.

6. The method of claim 1, further comprising the step of controlling the cutting tool to assume a non-extended state prior to the inserting step and before the retraction step.

7. The method of claim 6, wherein the tissue collection device assumes a closed configuration when the cutting tool assumes the non-extended state.

8. The method of claim 1, wherein the extension of the cutting tool is controlled by selectively and manually pushing and retracting a proximal end of the cutting tool in the distal and proximal directions, respectively.

9. The method of claim 1, wherein the cutting tool comprises an interior lumen and a plurality of through holes in fluid communication therewith, and wherein the method further comprises the step of delivering at least one fluid to the tissue via the plurality of through holes.

10. An imaging and treatment method for soft tissue, comprising the steps of:
   inserting a tubular member into the soft tissue, the tubular member including an ultrasonic transducer mounted within and near a distal end of the tubular member;
   rotating the tubular member within the soft tissue;
   displaying an output of the ultrasonic transducer on a display device; and
   acting upon the soft tissue based upon the displayed output.

11. The method of claim 10, wherein the ultrasonic transducer is tuned to within a frequency range of between about 7.5 MHz to about 20 MHz.

12. The method of claim 10, wherein the acting step includes a step of excising a selectively variable volume of soft tissue from a main tissue mass.

13. The method of claim 12, further including a step of collecting the excised volume of tissue in a tissue collection device mounted externally to the tubular member.

14. Method of excising a lesion from soft biological tissue using an excisional biopsy system including a generally tubular member having a cutting tool, a removable transducer core adapted to fit within the tubular member and an expandable sheath, comprising the steps of:
   fitting the transducer care through the expandable sheath,
   inserting the transducer and sheath though an incision in the tissue;
   imaging a target site within the tissue by energizing the transducer core,
   removing the transducer core from sheath while leaving the sheath in place within the tissue;
   securing the core within the generally tubular member so the core faces outwardly from the tubular member;
   sliding the tubular member through the expandable sheath until the cutting tool is positioned adjacent the lesion;
   cutting the lesion with the cutting tool; and
   retracting at least the tubular member from the incision.

15. The method of claim 14, further comprising the step of stabilizing the breast in one of an uncompressed and a slightly expanded state prior to the inserting step.

16. The method of claim 14, wherein the sheath remains within the tissue after the retracting step and wherein the method further comprises the step of:
   re-inserting the transducer core within the sheath and imaging the target site to insure that the lesion has been excised.

17. The method of claim 14, further comprising the step of collecting the cut lesion within an external tissue collection device secured to the tubular member.

18. The method of claim 14, wherein both the tubular member and the sheath are retracted from the incision.

* * * * *